US007074216B2

(12) United States Patent
Fowles et al.

(10) Patent No.: US 7,074,216 B2
(45) Date of Patent: Jul. 11, 2006

(54) SLIDING RECONSTITUTION DEVICE FOR A DILUENT CONTAINER

(75) Inventors: Thomas A. Fowles, McHenry, IL (US); Robert J. Weinberg, Richmond, IL (US); Thomas J. Progar, Spring Grove, IL (US)

(73) Assignee: Baxter International Inc., Deerfield, IL (US)

(*) Notice: Subject to any disclaimer, the term of this patent is extended or adjusted under 35 U.S.C. 154(b) by 187 days.

(21) Appl. No.: 10/106,716

(22) Filed: Mar. 26, 2002

(65) Prior Publication Data

US 2002/0123736 A1 Sep. 5, 2002

Related U.S. Application Data

(63) Continuation-in-part of application No. 09/561,666, filed on May 2, 2000, now Pat. No. 6,582,415, which is a continuation of application No. 09/153,816, filed on Sep. 15, 1998, now Pat. No. 6,113,583.

(51) Int. Cl.
*A61B 19/00* (2006.01)

(52) U.S. Cl. ...................... 604/413; 604/414; 604/415; 604/416

(58) Field of Classification Search ................ 604/403, 604/411–416, 200–201, 88, 533–535, 264, 604/86, 905, 107–110, 187, 192, 198, 239, 604/194, 82, 87; 137/614.04; 215/247; 220/265, 267; 403/83, 86, 326, 359.5
See application file for complete search history.

(56) References Cited

U.S. PATENT DOCUMENTS

| | | | | |
|---|---|---|---|---|
| 2,362,025 A | | 11/1944 | Price | |
| 3,230,954 A | | 1/1966 | Burgess et al. | |
| 3,330,281 A | | 7/1967 | Visser | |
| 3,330,282 A | | 7/1967 | Visser et al. | |
| 3,336,924 A | | 8/1967 | Sarnoff et al. | |
| 3,785,481 A | | 1/1974 | Allet-Coche | |
| 3,796,303 A | | 3/1974 | Allet-Coche | |
| 3,809,225 A | | 5/1974 | Allet-Coche | |
| 3,902,489 A | | 9/1975 | Carter | |
| 3,917,063 A | | 11/1975 | Chibret et al. | |
| 4,014,330 A | | 3/1977 | Genese | |
| 4,031,895 A | | 6/1977 | Porter | |
| 4,059,112 A | | 11/1977 | Tischlinger | |
| 4,116,196 A | | 9/1978 | Kaplan et al. | |
| 4,170,994 A | | 10/1979 | Komatsu | |
| 4,210,142 A | | 7/1980 | Wörder | |
| 4,210,173 A | | 7/1980 | Choksi et al. | |
| 4,226,330 A | | 10/1980 | Butler | |
| 4,243,080 A | | 1/1981 | Choksi et al. | |
| 4,247,651 A | | 1/1981 | Ohno et al. | |
| 4,264,667 A | * | 4/1981 | Murakami et al. | 428/195.1 |
| 4,270,533 A | | 6/1981 | Andreas | |
| 4,303,071 A | | 12/1981 | Smith | |
| 4,328,802 A | | 5/1982 | Curley et al. | |
| 4,392,850 A | | 7/1983 | Elias et al. | |
| 4,396,383 A | | 8/1983 | Hart | |
| 4,410,321 A | | 10/1983 | Pearson et al. | |
| 4,411,358 A | | 10/1983 | Bennwik et al. | |
| 4,411,662 A | | 10/1983 | Pearson | |
| 4,424,056 A | | 1/1984 | Urquhart et al. | |
| 4,424,057 A | | 1/1984 | House | |
| 4,432,754 A | | 2/1984 | Urquhart et al. | |
| 4,432,755 A | | 2/1984 | Pearson | |
| 4,432,756 A | | 2/1984 | Urquhart et al. | |
| 4,439,182 A | | 3/1984 | Huang | |
| 4,439,183 A | | 3/1984 | Theeuwes | |
| 4,458,733 A | | 7/1984 | Lyons | |
| 4,458,811 A | | 7/1984 | Wilkinson | |
| 4,465,471 A | | 8/1984 | Harris et al. | |
| 4,465,488 A | | 8/1984 | Richmond et al. | |
| 4,467,588 A | | 8/1984 | Carveth | |
| 4,469,872 A | | 9/1984 | Anderson et al. | |
| 4,474,574 A | | 10/1984 | Wolfe et al. | |
| 4,479,793 A | | 10/1984 | Urquhart et al. | |
| 4,479,794 A | | 10/1984 | Urquhart et al. | |
| 4,484,909 A | | 11/1984 | Urquhart et al. | |
| 4,484,920 A | | 11/1984 | Kaufman et al. | |
| 4,493,703 A | | 1/1985 | Butterfield | |
| 4,496,646 A | | 1/1985 | Ito | |
| 4,505,709 A | | 3/1985 | Froning et al. | |

4,507,113 A 3/1985 Dunlap
4,507,114 A 3/1985 Bohman et al.
4,511,351 A 4/1985 Theeuwes
4,511,352 A 4/1985 Theeuwes et al.
4,511,353 A 4/1985 Theeuwes
4,515,351 A 5/1985 Nakayama et al.
4,515,585 A 5/1985 Urquhart et al.
4,516,967 A 5/1985 Kopfer
4,516,977 A 5/1985 Herbert
4,518,386 A 5/1985 Tartaglia
4,519,499 A 5/1985 Stone et al.
4,521,211 A 6/1985 Theeuwes
4,525,162 A 6/1985 Urquhart et al.
4,533,348 A 8/1985 Wolfe et al.
4,534,757 A 8/1985 Geller
4,534,758 A 8/1985 Akers et al.
4,538,918 A 9/1985 Mittleman
4,539,793 A 9/1985 Malek
4,540,089 A 9/1985 Maloney
4,540,403 A 9/1985 Theeuwes
4,543,094 A 9/1985 Barnwell
4,543,101 A 9/1985 Crouch
4,548,598 A 10/1985 Theeuwes
4,548,599 A 10/1985 Urquhart et al.
4,548,606 A 10/1985 Larkin
4,550,825 A 11/1985 Sutryn et al.
4,552,277 A 11/1985 Richardson et al.
4,552,555 A 11/1985 Theeuwes
4,552,556 A 11/1985 Urquhart et al.
4,561,110 A 12/1985 Herbert
4,564,054 A 1/1986 Gustavsson
4,568,331 A 2/1986 Fischer et al.
4,568,336 A 2/1986 Cooper
4,568,346 A 2/1986 van Dijk
4,573,967 A 3/1986 Hargrove et al.
4,573,993 A 3/1986 Hoag et al.
4,576,211 A 3/1986 Valentini et al.
4,579,553 A 4/1986 Urquhart et al.
4,581,016 A 4/1986 Gettig
4,583,971 A 4/1986 Bocquet et al.
4,583,981 A 4/1986 Urquhart et al.
4,586,922 A 5/1986 Theeuwes
4,589,867 A 5/1986 Israel
4,589,879 A 5/1986 Pearson
4,590,234 A 5/1986 Tasaka et al.
4,596,555 A 6/1986 Theeuwes
4,601,704 A 7/1986 Larkin
4,602,910 A 7/1986 Larkin
4,606,734 A 8/1986 Larkin et al.
4,607,671 A 8/1986 Aalto et al.
4,608,043 A 8/1986 Larkin
4,610,684 A 9/1986 Knox et al.
4,613,326 A 9/1986 Szwarc
4,614,267 A 9/1986 Larkin
4,614,515 A 9/1986 Tripp et al.
4,623,334 A 11/1986 Riddell
4,629,080 A 12/1986 Carveth
4,630,727 A 12/1986 Feriani et al.
4,632,244 A 12/1986 Landau
4,637,934 A 1/1987 White
4,650,475 A 3/1987 Smith et al.
4,662,878 A 5/1987 Lindmayer
4,664,650 A 5/1987 Urquhart et al.
4,668,219 A 5/1987 Israel
4,675,020 A 6/1987 McPhee
4,692,144 A 9/1987 Carpenter
4,693,706 A 9/1987 Ennis, III
4,695,272 A 9/1987 Berglund et al.
4,703,864 A 11/1987 Larkin et al.
4,715,854 A 12/1987 Vaillancourt
4,717,388 A 1/1988 Steer et al.
4,722,733 A 2/1988 Howson
4,723,956 A 2/1988 Schnell et al.
4,727,985 A 3/1988 McNeirney et al.
4,731,053 A 3/1988 Hoffman
4,735,608 A 4/1988 Sardam
4,740,103 A 4/1988 Theeuwes
4,740,197 A 4/1988 Theeuwes
4,740,198 A 4/1988 Theeuwes
4,740,199 A 4/1988 Theeuwes
4,740,200 A 4/1988 Theeuwes
4,740,201 A 4/1988 Theeuwes
4,741,734 A 5/1988 Theeuwes
4,741,735 A 5/1988 Theeuwes
4,743,229 A 5/1988 Chu
4,747,834 A 5/1988 Prindle
4,752,292 A 6/1988 Lopez et al.
4,757,911 A 7/1988 Larkin et al.
4,759,756 A 7/1988 Forman et al.
4,778,453 A 10/1988 Lopez
4,781,679 A 11/1988 Larkin
4,782,841 A 11/1988 Lopez
4,784,259 A 11/1988 Grabenkort
4,784,658 A 11/1988 Grabenkort
4,785,858 A 11/1988 Valentini et al.
4,786,279 A 11/1988 Wilkinson et al.
4,787,429 A 11/1988 Valentini et al.
4,790,820 A 12/1988 Theeuwes
4,804,360 A 2/1989 Kamen
4,804,366 A 2/1989 Zdeb et al.
4,808,381 A 2/1989 McGregor et al.
4,816,024 A 3/1989 Sitar et al.
4,819,659 A 4/1989 Sitar
4,820,269 A 4/1989 Riddell
4,822,351 A 4/1989 Purcell
4,832,690 A 5/1989 Kuu
4,834,149 A 5/1989 Fournier et al.
4,834,152 A 5/1989 Howson et al.
4,842,028 A 6/1989 Kaufman et al.
4,850,978 A 7/1989 Dudar et al.
4,857,052 A 8/1989 Theeuwes
4,861,335 A 8/1989 Reynolds
4,861,585 A 8/1989 Galef, Jr. et al.
4,865,354 A 9/1989 Allen
4,871,354 A 10/1989 Conn et al.
4,871,360 A 10/1989 Theeuwes
4,871,463 A 10/1989 Taylor et al.
4,872,494 A 10/1989 Coccia
4,874,366 A 10/1989 Zdeb et al.
4,874,368 A 10/1989 Miller et al.
4,883,483 A 11/1989 Lindmayer
4,886,495 A 12/1989 Reynolds
4,898,209 A 2/1990 Zbed
4,906,103 A 3/1990 Kao
4,908,019 A 3/1990 Urquhart et al.
4,909,290 A 3/1990 Coccia
4,911,708 A 3/1990 Maezaki et al.
4,915,689 A 4/1990 Theeuwes
4,927,013 A 5/1990 Van Brunt et al.
4,927,423 A 5/1990 Malmborg
4,927,605 A 5/1990 Dorn et al.
4,931,048 A 6/1990 Lopez
4,936,445 A 6/1990 Grabenkort
4,936,829 A 6/1990 Zdeb et al.
4,936,841 A 6/1990 Aoki et al.
4,944,736 A 7/1990 Holtz
4,948,000 A 8/1990 Grabenkort
4,950,237 A 8/1990 Henault et al.
4,961,495 A 10/1990 Yoshida et al.
4,968,299 A 11/1990 Ahlstrand et al.
4,969,883 A 11/1990 Gilbert et al.
4,973,307 A 11/1990 Theeuwes
4,978,337 A 12/1990 Theeuwes
4,979,942 A 12/1990 Wolf et al.
4,982,875 A 1/1991 Pozzi et al.
4,983,164 A 1/1991 Hook et al.

| | | | |
|---|---|---|---|
| 4,985,016 A | 1/1991 | Theeuwes et al. | |
| 4,986,322 A | 1/1991 | Chibret et al. | |
| 4,994,029 A | 2/1991 | Rohrbough | |
| 4,994,031 A | 2/1991 | Theeuwes | |
| 4,994,056 A | 2/1991 | Ikeda | |
| 4,996,579 A | 2/1991 | Chu | |
| 4,997,083 A | 3/1991 | Loretti et al. | |
| 4,997,430 A | 3/1991 | Van der Heiden et al. | |
| 5,002,530 A | 3/1991 | Recker et al. | |
| 5,023,119 A | 6/1991 | Yamakoshi | |
| 5,024,657 A | 6/1991 | Needham et al. | |
| 5,030,203 A | 7/1991 | Wolf, Jr. et al. | |
| 5,032,117 A | 7/1991 | Motta | |
| 5,045,081 A | 9/1991 | Dysarz | |
| 5,049,129 A | 9/1991 | Zdeb et al. | |
| 5,049,135 A | 9/1991 | Davis | |
| 5,061,264 A | 10/1991 | Scarrow | |
| 5,064,059 A | 11/1991 | Ziegler et al. | |
| 5,069,671 A | 12/1991 | Theeuwes | |
| 5,074,844 A | 12/1991 | Zdeb et al. | |
| 5,074,849 A | 12/1991 | Sachse | |
| D323,389 S | 1/1992 | Aoki et al. | |
| 5,080,652 A | 1/1992 | Sancoff et al. | |
| 5,084,040 A | 1/1992 | Sutter | |
| 5,088,996 A | 2/1992 | Kopfer et al. | |
| 5,100,394 A | 3/1992 | Dudar et al. | |
| 5,102,408 A | 4/1992 | Hamacher | |
| 5,104,375 A | 4/1992 | Wolf et al. | |
| 5,114,004 A | 5/1992 | Isono et al. | |
| 5,114,411 A | 5/1992 | Haber et al. | |
| 5,116,315 A | 5/1992 | Capozzi et al. | |
| 5,116,316 A | 5/1992 | Sertic et al. | |
| 5,122,123 A | 6/1992 | Vaillancourt | |
| 5,125,892 A | 6/1992 | Drudik | |
| 5,125,908 A | 6/1992 | Cohen | |
| 5,126,175 A | 6/1992 | Yamakoshi | |
| 5,129,894 A | 7/1992 | Sommermeyer et al. | |
| 5,137,511 A | 8/1992 | Reynolds | |
| 5,147,324 A | 9/1992 | Skakoon et al. | |
| 5,152,965 A | 10/1992 | Fisk et al. | |
| 5,156,598 A | 10/1992 | Skakoon et al. | |
| 5,158,546 A | 10/1992 | Haber et al. | |
| 5,160,320 A | 11/1992 | Yum et al. | |
| 5,167,642 A | 12/1992 | Fowles | |
| 5,169,388 A | 12/1992 | McPhee | |
| 5,171,214 A | 12/1992 | Kolber et al. | |
| 5,171,219 A | 12/1992 | Fujioka et al. | |
| 5,171,220 A | 12/1992 | Morimoto | |
| 5,176,634 A | 1/1993 | Smith et al. | |
| 5,181,909 A | 1/1993 | McFarlane | |
| 5,186,323 A | 2/1993 | Pfleger | |
| 5,188,615 A | 2/1993 | Haber et al. | |
| 5,188,629 A | 2/1993 | Shimoda | |
| 5,195,658 A | 3/1993 | Hoshino | |
| 5,195,986 A | 3/1993 | Kamen | |
| 5,196,001 A | 3/1993 | Kao | |
| 5,199,947 A | 4/1993 | Lopez et al. | |
| 5,199,948 A | 4/1993 | McPhee | |
| 5,200,200 A | 4/1993 | Veech | |
| 5,201,705 A | 4/1993 | Berglund et al. | |
| 5,207,509 A | 5/1993 | Herbert | |
| 5,209,201 A | 5/1993 | Horie et al. | |
| 5,209,347 A | 5/1993 | Fabisiewicz et al. | |
| 5,211,201 A | 5/1993 | Kamen et al. | |
| 5,222,946 A | 6/1993 | Kamen | |
| 5,226,878 A | 7/1993 | Young | |
| 5,226,900 A | 7/1993 | Bancsi et al. | |
| RE34,365 E | 8/1993 | Theeuwes | |
| 5,232,029 A | 8/1993 | Knox et al. | |
| 5,232,109 A | 8/1993 | Tirrell et al. | |
| 5,246,142 A | 9/1993 | DiPalma et al. | |
| 5,247,972 A | 9/1993 | Tetreault | |
| 5,250,028 A | 10/1993 | Theeuwes et al. | |
| 5,257,985 A | 11/1993 | Puhl | |
| 5,257,986 A | 11/1993 | Herbert et al. | |
| 5,257,987 A | 11/1993 | Athayde et al. | |
| 5,259,843 A | 11/1993 | Watanabe et al. | |
| 5,259,954 A | 11/1993 | Taylor | |
| 5,261,902 A | 11/1993 | Okada et al. | |
| 5,267,646 A | 12/1993 | Inoue et al. | |
| 5,267,957 A | 12/1993 | Kriesel et al. | |
| 5,279,576 A | 1/1994 | Loo et al. | |
| 5,279,579 A | 1/1994 | D'Amico | |
| 5,279,583 A | 1/1994 | Shober, Jr. et al. | |
| 5,281,198 A | 1/1994 | Haber et al. | |
| 5,281,206 A | 1/1994 | Lopez | |
| 5,286,257 A | 2/1994 | Fischer | |
| 5,287,961 A | 2/1994 | Herran | |
| 5,289,585 A | 2/1994 | Kock et al. | |
| 5,302,603 A | 4/1994 | Crawley et al. | |
| 5,303,751 A | 4/1994 | Slater et al. | |
| 5,304,130 A | 4/1994 | Button et al. | |
| 5,304,163 A | 4/1994 | Bonnici et al. | |
| 5,304,165 A | 4/1994 | Haber et al. | |
| 5,306,242 A | 4/1994 | Joyce et al. | |
| 5,308,287 A | 5/1994 | Gunsing | |
| 5,308,347 A | 5/1994 | Sunago et al. | |
| 5,320,603 A | 6/1994 | Vetter et al. | |
| 5,328,464 A | 7/1994 | Kriesel et al. | |
| 5,330,048 A | 7/1994 | Haber et al. | |
| 5,330,426 A | 7/1994 | Kriesel et al. | |
| 5,330,450 A | 7/1994 | Lopez | |
| 5,330,462 A | 7/1994 | Nakamura | |
| 5,330,464 A | 7/1994 | Mathias et al. | |
| 5,332,399 A | 7/1994 | Grabenkort et al. | |
| 5,334,178 A | 8/1994 | Haber et al. | |
| 5,334,180 A | 8/1994 | Adolf et al. | |
| 5,334,188 A | 8/1994 | Inoue et al. | |
| 5,335,773 A | 8/1994 | Haber et al. | |
| 5,336,180 A | 8/1994 | Kriesel et al. | |
| 5,342,346 A | 8/1994 | Honda et al. | |
| 5,342,347 A | 8/1994 | Kikuchi et al. | |
| 5,344,414 A | 9/1994 | Lopez et al. | |
| 5,348,060 A | 9/1994 | Futagawa et al. | |
| 5,348,600 A | 9/1994 | Ishii | |
| 5,350,372 A * | 9/1994 | Ikeda et al. | 604/414 |
| 5,350,546 A | 9/1994 | Takeuchi et al. | |
| 5,352,191 A | 10/1994 | Sunago et al. | |
| 5,352,196 A | 10/1994 | Haber et al. | |
| 5,353,961 A | 10/1994 | Debush | |
| 5,356,380 A | 10/1994 | Hoekwater et al. | |
| 5,358,501 A | 10/1994 | Meyer | |
| 5,360,410 A | 11/1994 | Wacks | |
| 5,364,350 A | 11/1994 | Dittmann | |
| 5,364,369 A | 11/1994 | Reynolds | |
| 5,364,371 A | 11/1994 | Kamen | |
| 5,364,384 A | 11/1994 | Grabenkort et al. | |
| 5,364,386 A | 11/1994 | Fukuoka et al. | |
| 5,368,586 A | 11/1994 | Van Der Heiden et al. | |
| 5,370,164 A | 12/1994 | Galloway | |
| 5,373,966 A | 12/1994 | O'Reilly et al. | |
| 5,374,264 A | 12/1994 | Wadsworth, Jr. | |
| 5,376,079 A | 12/1994 | Holm | |
| 5,380,281 A | 1/1995 | Tomellini et al. | |
| 5,380,315 A | 1/1995 | Isono et al. | |
| 5,385,545 A | 1/1995 | Kriesel et al. | |
| 5,385,546 A | 1/1995 | Kriesel et al. | |
| 5,385,547 A | 1/1995 | Wong et al. | |
| 5,386,372 A | 1/1995 | Kobayashi et al. | |
| 5,393,497 A | 2/1995 | Haber et al. | |
| 5,397,303 A | 3/1995 | Sancoff et al. | |
| 5,398,851 A | 3/1995 | Sancoff et al. | |
| 5,401,253 A | 3/1995 | Reynolds | |
| 5,409,141 A | 4/1995 | Kikuchi et al. | |
| 5,423,421 A | 6/1995 | Inoue et al. | |
| 5,423,753 A | 6/1995 | Fowles et al. | |

| | | | | |
|---|---|---|---|---|
| 5,423,793 | A | | 6/1995 | Isono et al. |
| 5,423,796 | A | | 6/1995 | Shikhman et al. |
| 5,425,447 | A | | 6/1995 | Farina |
| 5,425,528 | A | | 6/1995 | Rains et al. |
| 5,429,256 | A | | 7/1995 | Kestenbaum |
| 5,429,603 | A | | 7/1995 | Morris |
| 5,429,614 | A | | 7/1995 | Fowles et al. |
| 5,435,076 | A | | 7/1995 | Hjertman et al. |
| 5,445,631 | A | | 8/1995 | Uchida |
| 5,458,593 | A | | 10/1995 | Macabasco et al. |
| 5,462,526 | A | | 10/1995 | Barney et al. |
| 5,470,327 | A | | 11/1995 | Helgren et al. |
| 5,472,022 | A | | 12/1995 | Michel et al. |
| 5,472,422 | A | | 12/1995 | Ljungquist |
| 5,474,540 | A | | 12/1995 | Miller et al. |
| 5,478,337 | A | * | 12/1995 | Okamoto et al. ........... 604/413 |
| 5,484,406 | A | | 1/1996 | Wong et al. |
| 5,484,410 | A | | 1/1996 | Kriesel et al. |
| 5,489,266 | A | | 2/1996 | Grimard |
| 5,490,848 | A | | 2/1996 | Finley et al. |
| 5,492,147 | A | | 2/1996 | Challender et al. |
| 5,492,219 | A | | 2/1996 | Stupar |
| 5,493,774 | A | | 2/1996 | Grabenkort |
| 5,494,190 | A | | 2/1996 | Boettcher |
| 5,501,887 | A | | 3/1996 | Tanaka et al. |
| 5,509,898 | A | | 4/1996 | Isono et al. |
| 5,510,115 | A | | 4/1996 | Breillatt, Jr. et al. |
| 5,514,090 | A | | 5/1996 | Kriesel et al. |
| 5,520,972 | A | | 5/1996 | Ezaki et al. |
| 5,522,804 | A | | 6/1996 | Lynn |
| 5,526,853 | A | | 6/1996 | McPhee et al. |
| 5,531,683 | A | | 7/1996 | Kriesel et al. |
| 5,533,389 | A | | 7/1996 | Kamen et al. |
| 5,533,973 | A | | 7/1996 | Piontek et al. |
| 5,533,994 | A | | 7/1996 | Meyer |
| 5,535,746 | A | | 7/1996 | Hoover et al. |
| 5,536,469 | A | | 7/1996 | Jonsson et al. |
| 5,538,506 | A | | 7/1996 | Farris et al. |
| 5,540,674 | A | | 7/1996 | Karas et al. |
| 5,547,471 | A | | 8/1996 | Thompson et al. |
| 5,554,125 | A | | 9/1996 | Reynolds |
| 5,554,128 | A | | 9/1996 | Hedges |
| 5,560,403 | A | | 10/1996 | Balteau et al. |
| 5,566,729 | A | | 10/1996 | Grabenkort et al. |
| 5,569,191 | A | | 10/1996 | Meyer |
| 5,569,192 | A | | 10/1996 | van der Wal |
| 5,573,527 | A | | 11/1996 | Macabasco et al. |
| 5,575,310 | A | | 11/1996 | Kamen et al. |
| 5,575,769 | A | * | 11/1996 | Vaillancourt ................. 604/86 |
| 5,577,369 | A | | 11/1996 | Becker et al. |
| 5,584,808 | A | | 12/1996 | Healy |
| 5,593,028 | A | | 1/1997 | Haber et al. |
| 5,595,314 | A | | 1/1997 | Weiler |
| 5,596,193 | A | | 1/1997 | Chutjian et al. |
| 5,603,695 | A | | 2/1997 | Erickson |
| 5,603,696 | A | | 2/1997 | Williams et al. |
| 5,605,542 | A | | 2/1997 | Tanaka et al. |
| 5,611,792 | A | | 3/1997 | Gustafsson |
| 5,620,434 | A | | 4/1997 | Brony |
| 5,624,405 | A | | 4/1997 | Futagawa et al. |
| 5,688,254 | A | | 11/1997 | Lopez et al. |
| 5,709,666 | A | | 1/1998 | Reynolds |
| 5,826,713 | A | | 10/1998 | Sunago et al. |
| 5,827,262 | A | | 10/1998 | Neftel et al. |
| 5,897,526 | A | | 4/1999 | Vaillancourt |
| 5,925,029 | A | | 7/1999 | Jansen et al. |
| 6,077,244 | A | * | 6/2000 | Botich et al. ............... 604/110 |
| 6,253,804 | B1 | | 7/2001 | Safabash |
| 6,378,714 | B1 | | 4/2002 | Jansen et al. ............... 215/249 |

FOREIGN PATENT DOCUMENTS

| | | | |
|---|---|---|---|
| DE | 1913926 | | 9/1970 |
| DE | 1766151 | | 6/1971 |
| EP | 0 022 977 | A1 | 1/1981 |
| EP | 0 091 310 | A2 | 10/1983 |
| EP | 0 126 718 | A2 | 11/1984 |
| EP | 0 285 424 | A1 | 10/1988 |
| EP | 0 335 378 | A2 | 10/1989 |
| EP | 0 345 230 | A2 | 12/1989 |
| EP | 0 363 770 | A1 | 4/1990 |
| EP | 0 395 758 | A1 | 11/1990 |
| GB | 1 419 061 | | 11/1972 |
| GB | 2 211 104 | A | 6/1989 |
| WO | WO 83/03540 | | 10/1983 |
| WO | WO 85/03432 | | 8/1985 |
| WO | WO 90/03536 | | 4/1990 |
| WO | WO 92/11897 | | 7/1992 |
| WO | WO 93/02723 | | 2/1993 |
| WO | WO 93/09825 | | 5/1993 |
| WO | WO 94/00094 | | 1/1994 |
| WO | WO 97/25015 | | 7/1997 |
| WO | WO 99/27886 | | 6/1999 |

* cited by examiner

*Primary Examiner*—Patricia Bianco
*Assistant Examiner*—Leslie R. Deak
(74) *Attorney, Agent, or Firm*—Austin J. Foley; Bell, Boyd & Lloyd LLC

(57) ABSTRACT

The present invention provides a reconstitution device (10) for placing a first container (12), such as a liquid container (e.g. flexible container or syringe), in fluid communication with a second container (14), such as a drug vial. To this end, there is provided a connector device (10) for establishing fluid communication between the diluent container (12) and the drug vial (14). The connector device (10) has a first sleeve member (32) having a first end (36) and a second end (38). The first sleeve member (32) has at the first end (36), a first attaching member (30) adapted to attach to the liquid container (12). The connector device (10) also has a second sleeve member (34) having a first end (48) and a second end (50). The second sleeve member (34) is movable axially with respect to the first sleeve member (32) from an inactivated position to an activated position. The second sleeve member (34) has a protuberance (66) on an inner surface of the second sleeve member (34). A second attaching member (28) is attached on the second end (50) of the second sleeve member (34) and is adapted to attach to the second container (14). The second attaching member (28) has a sealing member (84). A piercing member (76) is positioned in the chamber and projects within the sleeve members (32,34) for providing a fluid flow path from the first container (12) to the second container (14). The piercing member (76) is moveable from a first position in the inactivated position to a second position in the activated position wherein the piercing member (76) moves past the protuberance (66), the protuberance (66) preventing movement of the piercing member (76) back to the first position. The device (10) is movable from the inactivated position to the activated position by a force generally applied to the device outside the liquid container (12).

19 Claims, 18 Drawing Sheets

SLIDING RECONSTITUTION DEVICE FOR A DILUENT CONTAINER

RELATED APPLICATION

This is a continuation-in-part application of U.S. application Ser. No. 09/561,666, filed May 2, 2000 now U.S. Pat. No. 6,582,415, which is a continuation application of U.S. application Ser. No. 09/153,816, filed Sep. 15, 1998, now U.S. Pat. No. 6,113,583, patented Sep. 5, 2000, which applications are hereby incorporated herein by reference and made a part hereof.

TECHNICAL FIELD

The present invention relates generally to the delivery of a beneficial agent to a patient. More specifically, the present invention relates to an improved device for reconstituting a beneficial agent to be delivered to a patient.

BACKGROUND OF THE INVENTION

Many drugs are unstable even for a short period of time in a dissolved state and therefore are packaged, stored, and shipped in a powdered or lyophilized state to increase their shelf life. In order for powdered drugs to be given intravenously to a patient, the drugs must first be placed in liquid form. To this end, these drugs are mixed or reconstituted with a diluent before being delivered intravenously to a patient. The diluents may be, for example, a dextrose solution, a saline solution, or even water. Typically the drugs are stored in powdered form in glass vials or ampules.

Other drugs, although in a liquid state, must still be diluted before administering to a patient. For example, some chemotherapy drugs are stored in glass vials or ampules, in a liquid state, but must be diluted prior to use. As used herein, reconstitution means to place the powdered drug in a liquid state, as well as, the dilution of a liquid drug.

The reconstitution procedure should be performed under sterile conditions. In some procedures for reconstituting, maintaining sterile conditions is difficult. Moreover, some drugs, such as chemotherapy drugs, are toxic and exposure to the medical personnel during the reconstitution procedure can be dangerous. One way of reconstituting a powdered drug is to inject the liquid diluent directly into the drug vial. This can be performed by use of a combination-syringe and syringe needle having diluent therein. In this regard, drug vials typically include a pierceable rubber stopper. The rubber stopper of the drug vial is pierced by the needle, and liquid in the syringe is then injected into the vial. The vial is shaken to mix the powdered drug with the liquid. After the liquid and drug are mixed, a measured amount of the reconstituted drug is then drawn into the syringe. The syringe is then withdrawn from the vial and the drug can then be injected into the patient. Another method of drug administration is to inject the reconstituted drug, contained in the syringe, into a parenteral solution container. Examples of such containers include a MINI-BAG™ flexible parenteral solution container or VIAFLEX® flexible parenteral solution container sold by Baxter Healthcare Corporation of Deerfield, Ill. These parenteral solution containers may already have therein dextrose or saline solutions. The reconstituted drug is injected into the container, mixed with the solution in the parenteral solution container and delivered through an intravenous solution administration set to a vein access site of the patient.

Another method for reconstituting a powdered drug utilizes a reconstitution device sold by Baxter Healthcare Corporation, product code No. 2B8064. That device includes a double pointed needle and guide tubes mounted around both ends of the needle. This reconstitution device is utilized to place the drug vial in fluid communication with a flexible-walled parenteral solution container. Once the connection is made by piercing a port of the flexible container with one end of the needle and the vial stopper with the other end of the needle, liquid in the solution container may be forced through the needle into the drug vial by squeezing the sidewalls of the solution container. The vial is then shaken to mix the liquid and drug. The liquid in the vial is withdrawn by squeezing air from the solution container into the vial. When compression of the flexible walled solution container is stopped, the pressurized air in the vial acts as a pump to force the liquid in the vial back into the solution container.

An improvement to this product is the subject of commonly assigned U.S. Pat. No. 4,607,671 to Aalto et al. The device of the '671 patent includes a series of bumps on the inside of a sheath to grip a drug vial. These bumps hinder the inadvertent disconnection of the device with the vial.

U.S. Pat. No. 4,759,756 discloses a reconstitution device which, in an embodiment, includes an improved vial adaptor and bag adaptor that permit the permanent coupling of a vial and liquid container. The bag adaptor is rotatable relative to the vial adaptor to either block fluid communication in a first position or effect fluid communication in a second position.

Another form of reconstitution device is seen in commonly assigned U.S. Pat. No. 3,976,073 to Quick et al. Yet another type of reconstitution device is disclosed in U.S. Pat. No. 4,328,802 to Curley et al., entitled "Wet-Dry Syringe Package" which includes a vial adaptor having inwardly directed retaining projections to firmly grip the retaining cap lip of a drug vial to secure the vial to the vial adaptor. The package disclosed by Curley et al. is directed to reconstituting a drug by use of a liquid-filled syringe.

Other methods for reconstituting a drug are shown, for example, in commonly assigned U.S. Pat. No. 4,410,321 to Pearson et al., entitled "Close Drug Delivery System"; U.S. Pat. Nos. 4,411,662 and 4,432,755 to Pearson, both entitled "Sterile Coupling"; U.S. Pat. No. 4,458,733 to Lyons entitled "Mixing Apparatus"; and U.S. Pat. No. 4,898,209 to Zdeb entitled "Sliding Reconstitution Device With Seal."

Other related patents include U.S. Pat. No. 4,872,867 to Kilinger entitled "Wet-Dry Additive Assembly"; U.S. Pat. No. 3,841,329 to Kilinger entitled "Compact Syringe"; U.S. Pat. No. 3,826,261 to Kilinger entitled "Vial and Syringe Assembly"; U.S. Pat. No. 3,826,260 to Kilinger entitled "Vial and Syringe Combination"; U.S. Pat. No. 3,378,369 to Kilinger entitled "Apparatus for Transferring Liquid Between a Container and a Flexible Bag"; and German specification DE OS 36 27 231.

Commonly assigned U.S. Pat. No. 4,898,209 to Zdeb (the '209 Patent), discloses a sliding reconstitution device which solved some of the problems discussed above. For example, the connector allowed for preattaching the device to a vial without piercing a closure of the vial. However, no seal was provided on the opposite end of the connector so the vial and device assembly had to be used immediately after connection or stored in a sterile environment, such as under a hood.

The '209 Patent discloses a first sleeve member that is mounted concentrically about a second sleeve member. The sleeve members can be moved axially with respect to each other to cause a needle or cannula to pierce a drug container and a diluent container to place the containers in fluid communication with each other.

The process for using the '209 connector required three distinct steps. The sleeves had to be rotated with respect to one another to move the device into an unlocked position. The sleeves were then moved axially with respect to one another to an activated position to pierce closures of the containers. The sleeves had to be rotated again to lock the sleeves in the activated position.

However, it is possible for the device of the '209 Patent to be easily and inadvertently disassembled when being moved to the activated position. The second sleeve is capable of sliding entirely though the first sleeve member and becoming disassociated into separate parts. This would require the medical personnel to either reassemble the device or dispose of it due to contamination.

Also, the device of the '209 Patent did not provide for a visual indication that the device was in the activated position. It was also possible for the device to be inadvertently moved to the inactivated position, by rotating the first and second sleeve members in a direction opposite of the third step described above.

Additionally, it was possible for the second container, which is frequently a vial, to rotate within the device. This could cause coring of the vial stopper which could lead to leakage of the vial stopper. Additionally it was possible for a vial to be misaligned while being attached to the device causing the attachment process to be difficult for medical personnel. Further, the connector only releasably attached to the vial. Removal of the vial could remove all tamper evident indications that the reconstitution step has occurred and could lead to a second unintended dosage of medicine to be administered. Finally, the seal had a sleeve that covered only a portion of the cannula. The sleeve of the seal was relatively resilient and had the tendency of pushing the connector away from the drug container when docked thereto.

Yet another connector for attaching a drug vial to a parenteral solution container is disclosed in U.S. Pat. No. 4,675,020 ("the '020 patent"). The '020 patent discloses a connector having an end that docks to a drug vial and an opposite end that connects to the solution container. A shoulder and an end surface of the vial are held between first and second jaws of the vial end of the connector. The second jaws 71 terminate in a relatively sharp point that digs into and deforms the outermost end surface 94 of the vial sufficiently to accommodate dimensional variations between the shoulder and the outermost end surface of the vial. The marks that are left in the deformable end surface of the vial are intended to provide a tamper evident feature. However, tamper evident marks will not be left in vials that have a cap that is too short to impinge upon the sharp points.

The connector has a spike 25 that penetrates stoppers on the vial and on the solution container to place these containers in fluid communication. However, because the spike 25 extends outward beyond skirt sections 57, the connector of the '020 patent cannot be preattached to the fluid container or the drug container without piercing the stoppers of each. (The '020 patent states that the connector may be preassembled onto a drug vial, but there is no explanation of the structure of such a device. (Col. 6, lines 40–49)). This is undesirable as it initiates the time period in which the drug must be used, and typically this is a short period relative to the normal shelf-life of the product.

Also, the connector of the '020 patent does not provide a structure for preventing a docked vial from rotating. A closure of the vial can become damaged or cored upon rotation, which in turn, can lead to particles from the closure from entering the fluid that eventually passes to a patient. It can also lead to leakage of the closure of the vial.

Another connector for attaching a drug vial to a flexible container is disclosed in commonly assigned U.S. patent application Ser. No. 08/986,580. This connector has a piercing member mounted between two sleeves slidably mounted to one another. The bag connecting end is sealed by a peelable seal material. The seal material must be removed before connecting to the flexible container. Removal of the seal material exposes the piercing member to the outside environment thereby breaching the hermetic seal of the piercing member.

Another connector for attaching a drug vial to a flexible solution container is disclosed in U.S. Pat. No. 5,352,191 ("the '191 Patent"). The connector has a communicating portion having a communicating passage disposed at a top portion of the flexible container wherein one end of the communicating portion extends into the flexible container. The drug vial is fitted partially or wholly into an opposite end of the communicating portion. A membrane is disposed in the communicating passage for closing the passage. The connector also includes a puncturing needle unit mounted in the communicating passage for enabling the drug vial and flexible container to communicate with each other. When the puncturing needle unit is pressed externally through the flexible container, the needle breaks the membrane and opening of the drug vial to enable the drug vial and container to communicate with each other.

U.S. Pat. No. 5,380,315 and EP 0843992 disclose another connector for attaching a drug vial to a flexible solution container. Similar to the '191 patent, this patent and patent application have a communication device in the form of spike that is mounted within the flexible container. The communication device is externally pressed towards a drug vial to puncture the drug vial and communicate the drug vial with the flexible container.

U.S. Pat. No. 5,478,337 discloses a device for connecting a vial to a flexible container. This patent requires the vial to be shipped pre-assembled to the connector, and, therefore, does not allow for medical personnel to selectively attach a vial to the connector.

Finally, U.S. Pat. No. 5,364,386 discloses a device for connecting a vial to a medical fluid container. The device includes a screw cap 32 that must be removed before inserting the vial. Removing the screw cap, however, potentially exposes the piercing member 48 to contaminants as the piercing member is not hermetically sealed.

The present invention is provided to solve these and other problems.

SUMMARY OF THE INVENTION

The present invention provides a fluid reconstitution device for placing a first container, such as a diluent or liquid container (e.g. flexible container or syringe), in fluid communication with a second container, such as a drug vial. To this end, there is provided a connector device for establishing fluid communication between the liquid container and the drug vial. The connector has a piercing member having a first end and a second end and a central fluid pathway. The piercing member is mounted to the liquid container and has fluid accessing portions hermetically sealed from an outside environment. A vial receiving chamber is associated with the piercing member and is dimensioned to connect to the vial. The vial may be selectively attached to the device without piercing the closure of the vial and without breaching the hermetic seal of the fluid accessing portions of the piercing member. Means are provided for connecting the vial receiving chamber to the liquid container. The device is movable from an inactivated position, where the piercing member is outside the sidewalls and no fluid flows between the liquid container and the drug vial, to an activated position, where fluid flows through the fluid pathway between the liquid container and the drug vial. The device is movable from the inactivated position to the activated position by a force applied to the device outside the liquid container.

According to another aspect of the invention, there is provided a hub mounting the piercing member within the means for connecting the vial receiving chamber to the liquid container and a protuberance attached to the means for connecting the vial receiving chamber to the liquid container and dimensioned for allowing movement of the hub from a first position to a second position wherein the hub moves past the protuberance. When the device is moved from the activated position to a deactivated position, the protuberance prevents the hub from returning to the first position.

According to another aspect of the invention, there is provided a tamper evident strip associated with the device for indicating when the device has been moved from the inactivated position to the activated position.

According to another aspect of the invention, the device has a first attaching member in the form of a port connector having a port snap connected to a port sleeve. The port snap has a flange extending from an outer surface and is connected to a first sleeve member wherein the flange engages a protrusion on the first sleeve member. The port sleeve is adapted to attach to the liquid container. The port sleeve preferably has a membrane at one end.

According to yet another aspect of the invention, the device includes a gripper assembly attached to the second end of the second sleeve. The gripper assembly has a base and an annular wall portion extending from the base and a plurality of fingers circumjacent the wall portion. The fingers are circumferentially spaced defining a vial receiving chamber adapted to receive the vial, wherein one finger has a tab adapted to engage an underside of the neck and one finger has a standing rib adapted to engage a side portion of the vial closure. A first annular rim extends from the base and a second annular rim extends collectively from the fingers and in spaced relation to the first annular rim.

According to a further aspect of the invention, the gripper assembly has a disk-shaped panel extending to bottom portions of the fingers. The panel has a center opening therethrough and supports an annular rim extending from the panel. The annular rim is adapted to form a fluid tight seal against a target site of a closure of a container.

According to another aspect of the invention, there is provided a sealing member preferably in the form of a septum having a disk having opposing first and second surfaces. The disk has a center hub having a generally thickened cross-section. The first surface has a first annular groove receiving the first annular rim. The second surface has a second annular groove receiving the second annular rim. The second surface further has an annular ridge having a sidewall tapering axially-outwardly, so that the annular ridge is capable of forming a fluid tight seal with the vial when the vial is received by the fingers of the gripper assembly.

According to another aspect of the invention, the thickened center hub substantially blocks the central fluid passageway of the piercing member as the center hub is penetrated by the piercing member but before the piercing member completely penetrates the piercing center hub.

According to a further aspect of the invention, a septum is provided that includes a cap positioned within the annular ridge. The cap is adapted to provide a fluid tight seal against a target site of a closure of a container.

According to yet another aspect of the invention, the septum could include structure to provide a dual seal against the closure of the container.

According to yet another aspect of the invention, the septum can take various forms and have rigid or flexible portions.

Other features and advantages of the invention will become apparent from the following description taken in conjunction with the following drawings.

DETAILED DESCRIPTION OF THE PREFERRED EMBODIMENTS

Figure 1:
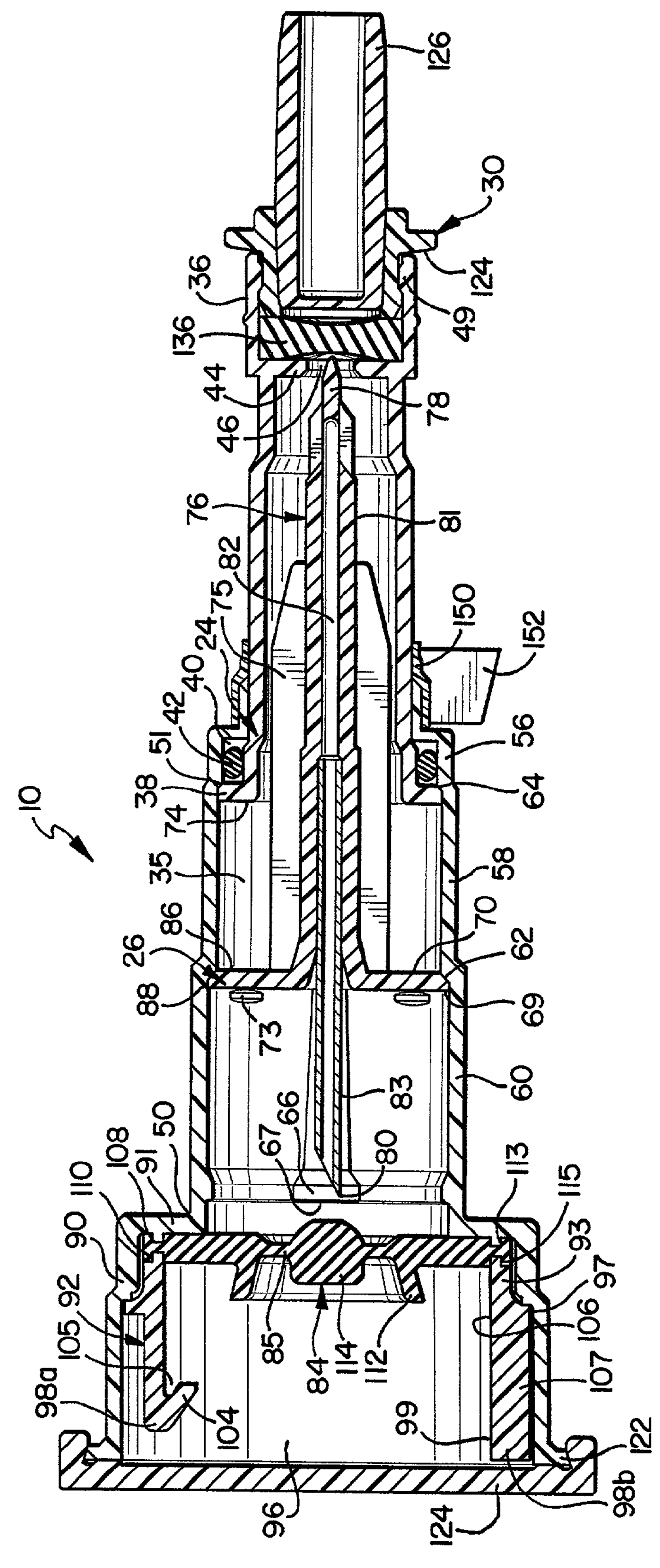
FIG. 1 is a cross-sectional elevation view of a connector device of the present invention.

While the invention is susceptible of embodiment in many different forms, there is shown in the drawings and will herein be described in detail preferred embodiments of the invention. It is to be understood that the present disclosure is to be considered as an exemplification of the principles of the invention. This disclosure is not intended to limit the broad aspect of the invention to the illustrated embodiments.

The present invention provides a connector device that is used to mix two substances within separate containers. More particularly, the invention provides a device to reconstitute a drug with a diluent. To accomplish the reconstitution of the drug, the invention provides an improved connecting device for attaching to a first container, commonly a flexible bag or a syringe, containing a diluent, to a second container, commonly a vial containing a drug to be reconstituted. The connector provides fluid communication between the two containers through a hermetically sealed piercing member so that the drug may be reconstituted, and delivered to a patient. What is meant by hermetically sealed is that the portions of the piercing member that contact the fluid and that pierce the closures of the two containers are sealed from the outside environment.

While the diluent will be a liquid, the beneficial agent may be either a powder or a lyophilized drug to be dissolved or a liquid drug to be reduced in concentration. The devices of the present invention provide the benefit of allowing medical personnel to selectively attach a vial of their choice to the connector. Thus, hospitals and pharmacies do not have to stock prepackaged drug vial and connector assemblies. Further, the connectors of the present invention allow for docking a vial to the connector without breaching the hermetic seal of a piercing member associated with the connector and without piercing the closure of the vial. Thus, a vial may be pre-docked to the device of the present invention for essentially the full period the drug is active. Further, the device of the present invention can be activated by applying a force directly to the connector without necessarily contacting sidewalls of the first and second containers.

Figure 2:
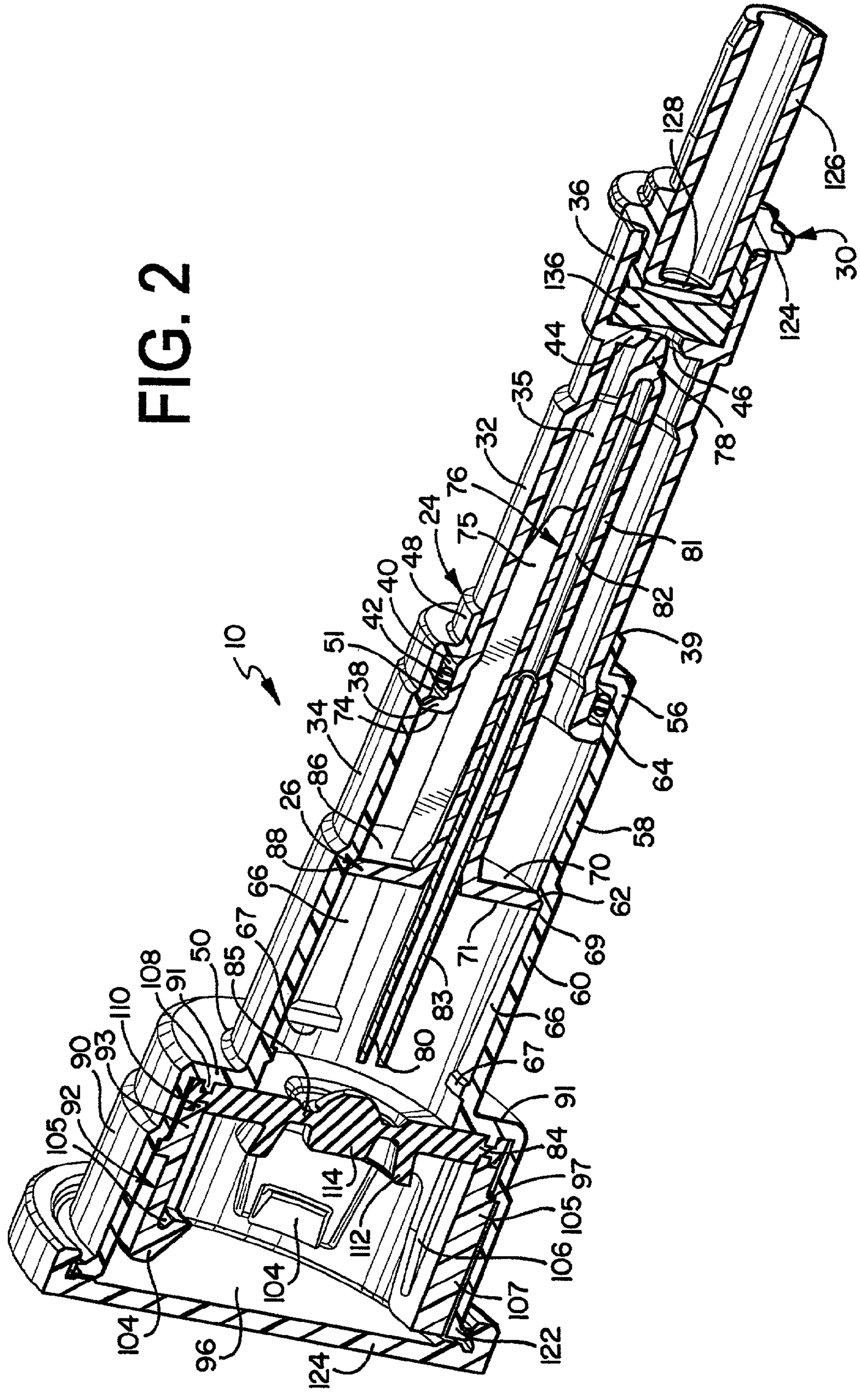
FIG. 2 is a cross-sectional perspective view of the connector device of the present invention.
Figure 4:
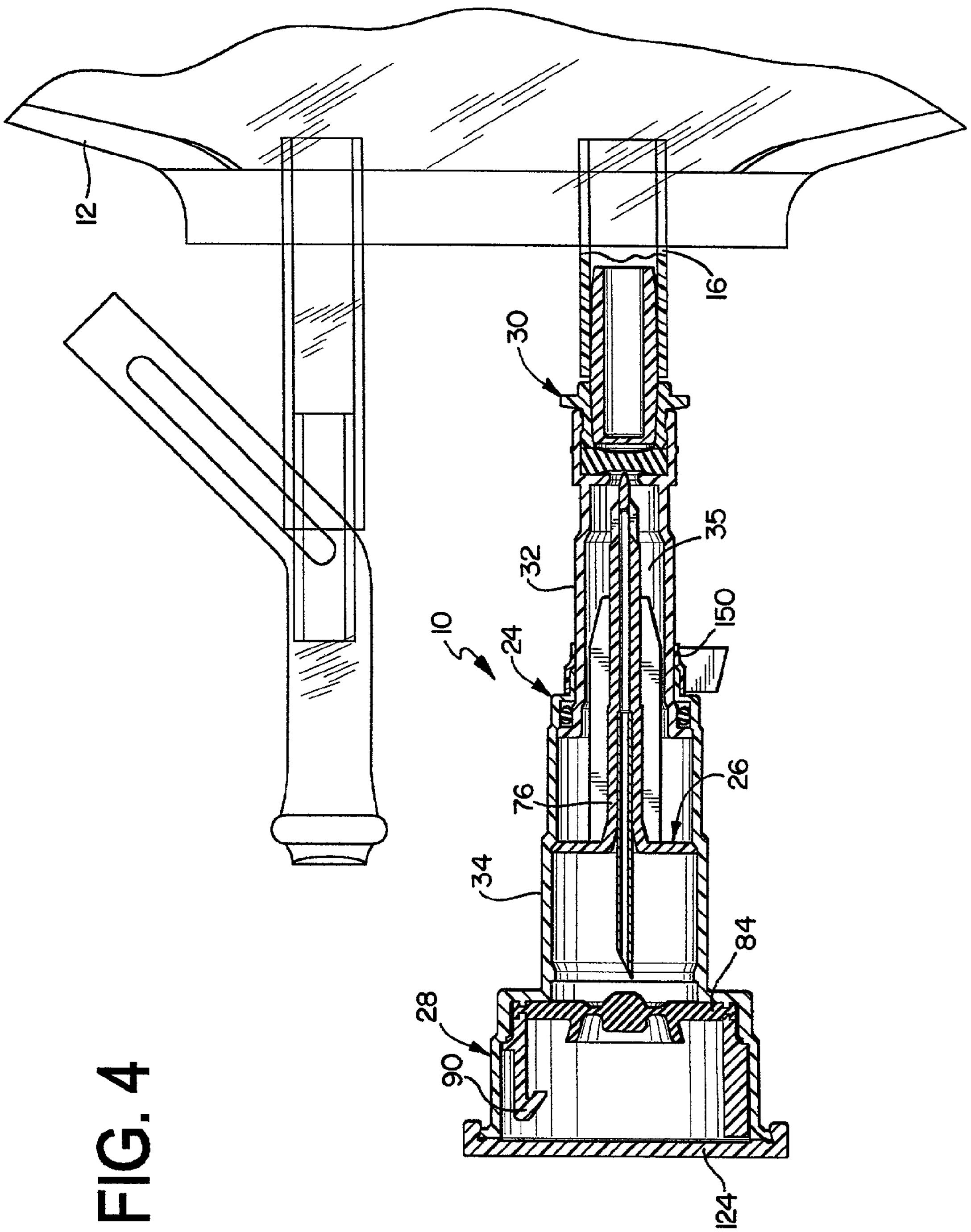
FIG. 4 is a cross-sectional view of the connector device of the present invention attached to a flexible container.

Referring to FIGS. 1, 2 and 4, a connector device is disclosed and generally referred to with the reference numeral 10. The device 10 is adapted to place a first container 12, containing a liquid to be used as a diluent, in fluid communication with a second container 14, containing a drug to be diluted or reconstituted.

The first container 12 is typically a flexible bag and is used to contain solutions for a patient to be received intravenously. Flexible containers are typically constructed from two sheets of a polymeric material forming sidewalls that are attached at their outer periphery to define a fluid tight chamber therebetween. In a preferred form of the invention, the fluid container is a coextruded layered structure having a skin layer of a polypropylene and a radio frequency susceptible layer of a polymer blend of 40% by weight polypropylene, 40% by weight of an ultra-low density polyethylene, 10% by weight of a dimer fatty acid polyamide and 10% by weight of a styrene-ethylene-butene-styrene block copolymer. These layered structures are more thoroughly set forth in commonly assigned U.S. Pat. No. 5,686,527 which is incorporated herein by reference and made a part hereof. At one point on the periphery of the container 12 a tubular port 16 is inserted between the sidewalls to provide access to the fluid chamber. A second port 18 is shown for allowing access by a fluid administration set to deliver the reconstituted drug to a patient. However, the first container 12 can be any type of container, including, for example, a syringe barrel, suitable for containing a liquid to be used to reconstitute a drug.

The second container 14 (FIG. 5), which contains a drug to be reconstituted, is a vial. The vial 14 is typically a glass container with a closure member. The closure member may include a rubber stopper 20 and may also have a crimp ring 22. The rubber stopper 20 is inserted in an opening of the vial 14. The rubber stopper 20 is held in place by the crimp ring 22 (FIG. 3), typically made of soft metal such as aluminum, that is crimped around the stopper 20 and the neck of the vial 14 to fixedly attach the stopper 20 to the vial 14. The crimp ring 22 has an aperture to define a target site on the rubber stopper 20. The device 10 can be adapted to accept vials of any size, particularly 20 mm and 13 mm vials. Additionally, the second container 14 can be any container that is adapted to accommodate drugs that require reconstitution.

Figure 7:
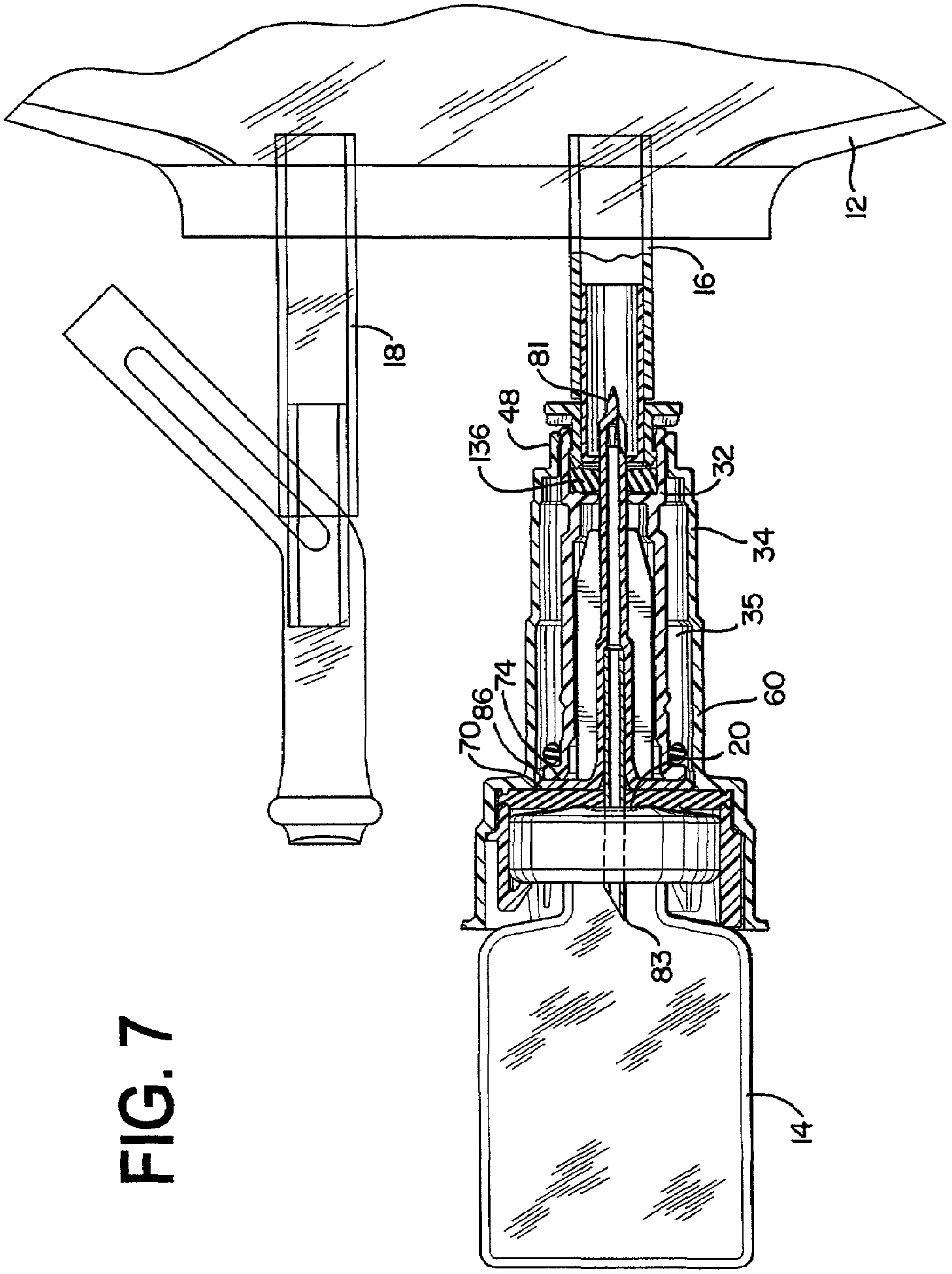
FIG. 7 is a cross-sectional view of the connector device in an activated position.
Figure 8:
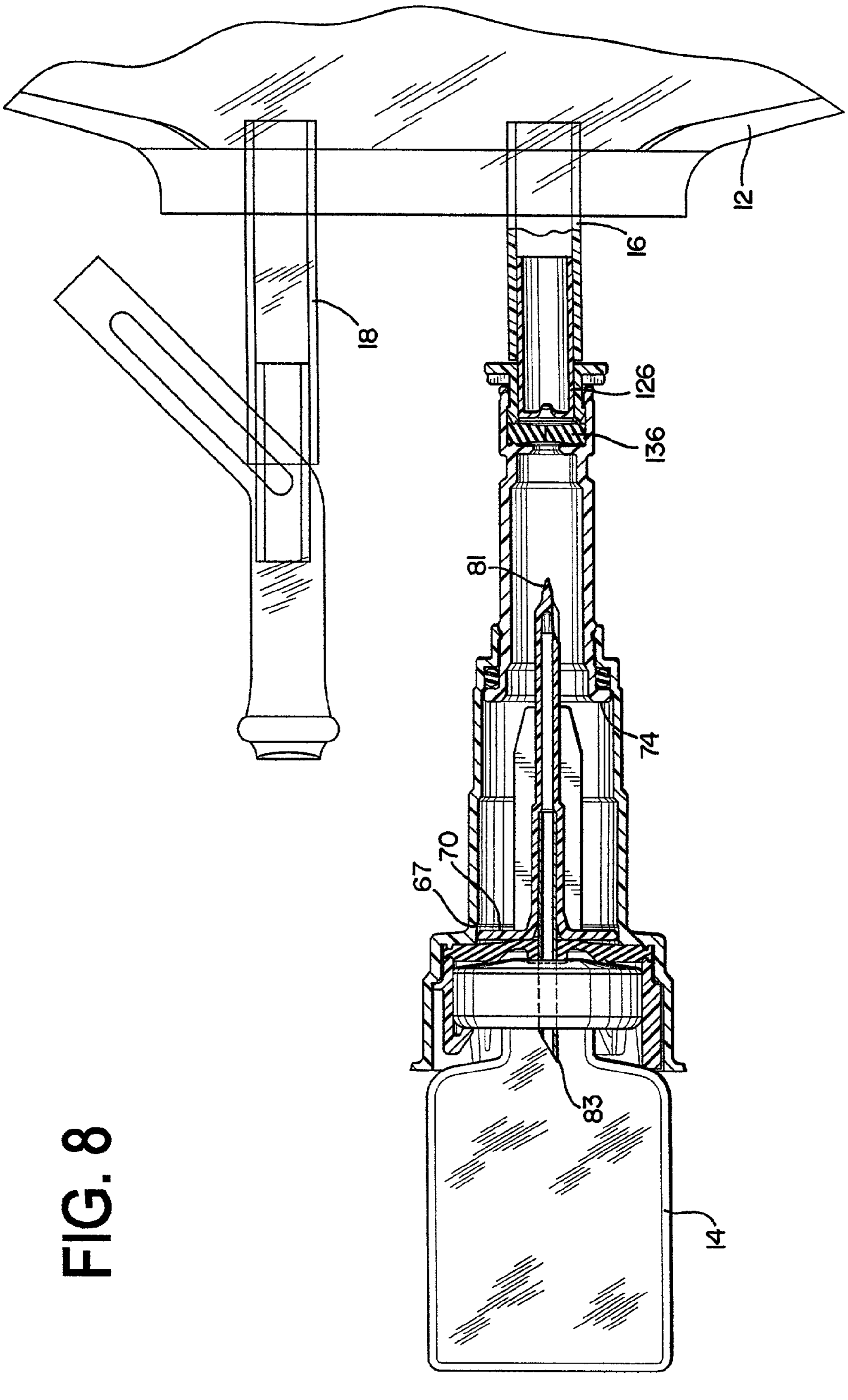
FIG. 8 is a cross-sectional view of the connector device in a deactivated position.

The connector 10, as stated above, is adapted to connect to both the flexible bag 12 and the vial 14 and place the contents of the flexible bag 12 and the vial 14 into fluid communication with one another. As shown in FIGS. 1, 2 and 4, the connector 10 generally comprises a sleeve assembly 24, a piercing assembly 26, a gripper assembly 28 and a port connector assembly 30. As described in greater detail below, the gripper assembly 28 and one portion of the sleeve assembly 24 are collectively adapted for axial movement with respect to another portion of the sleeve assembly 24 from an inactivated position (e.g., FIG. 5) to an activated position (FIG. 7). What is meant by the inactivated position is that the containers 12,14 are not in fluid communication with each other wherein the connector 10 has not been activated. What is meant by the activated position is that the containers 12,14 are placed in fluid communication with each other. What is meant by the deactivated position, or post reconstitution position, is the first container 12 and the second container 14 are not in fluid communication and have been moved from the activated position to the deactivated position (FIG. 8).

As is further shown in FIGS. 1 and 2, the sleeve assembly 24 generally comprises a first sleeve 32 and a second sleeve 34. The first sleeve 32 and second sleeve 34 are mounted for translational motion with respect to one another from the inactivated position to the activated position. In a preferred form of the invention, the first sleeve 32 is slidably mounted within the second sleeve 34. Each sleeve 32,34 has generally cylindrical walls and, collectively, the sleeves 32,34 define a central passageway 35 through the connector 10.

Figure 3:
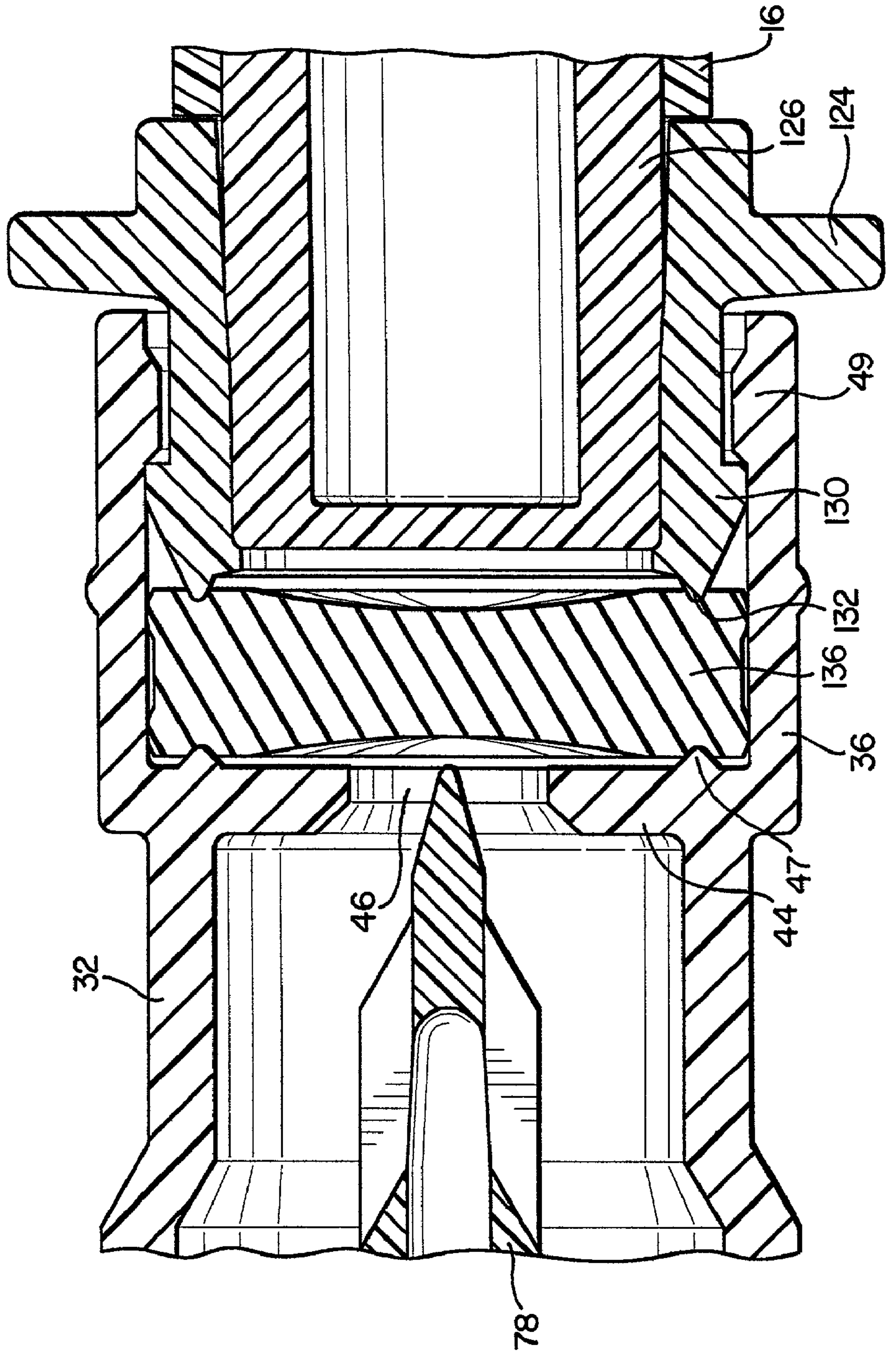
FIG. 3 is an enlarged partial cross-sectional view of a port connector assembly of the connector device of FIG. 1.

The first sleeve 32 has a first end 36 and a second end 38. The first end 36 is adapted to receive and be connected to the port connector 30 as described in greater detail below. The second end 38 of the first sleeve 32 has a partial annular groove 40. The annular groove 40 receives a sealing member 42, preferably in the form of an O-ring. The sealing member 42 provides a seal between the first sleeve 32 and the second sleeve 34 and in a preferred form of the invention is disposed between the first sleeve 32 and the second sleeve 34. Of course, other sealing members such as gaskets, washers and similar devices could be used to achieve a seal between the sleeves 32,34 as is well known in the art and without departing from the present invention. Optionally, the second sleeve 34 could incorporate the annular groove 40 for retaining the sealing member 42. The first sleeve 32 further has a guide 44 at an inner surface of the sleeve 32, intermediate of the first end 36 and the second end 38. The guide 44 has an opening 46 adapted to receive a portion of the piercing assembly 26 during activation. As shown in FIG. 3, a projection 47 extends from the guide 44. An inner surface of the first sleeve 32 has a ramped protrusion 49 extending preferably around a full periphery of the inner surface. The protrusion 49 will cooperate with the port connector 30 as described below.

Additionally, as shown in FIGS. 1 and 2, the first sleeve 32 has a stop surface 51 that cooperates with a stop surface in the form of the second ledge 64 on the second sleeve 34 to prevent the first sleeve 32 from sliding out of the second sleeve 34. The first sleeve 32 also has a stop surface 74 that interfaces with the piercing assembly 26, as will be described in greater detail below. Finally, as shown in FIG. 2, the first sleeve has a detent 39 on its outer surface. The detent 39 cooperates with an end of the second sleeve 34 which maintains the device in the inactivated position.

As shown in FIGS. 1 and 2, the second sleeve 34 also has a first end 48 and a second end 50. The second end 50 of the second sleeve 34 is connected to the gripper assembly 28. In a preferred embodiment, the gripper assembly 28 is an integral portion of the second sleeve 34 although it could be separately attached. The second sleeve 34 accommodates the piercing assembly 26 within the central passageway 35. The piercing assembly 26 is slidable within the central passageway 35 along an inner surface of the second sleeve 34. Also, as shown in FIG. 2, the second sleeve 34 has a first section 56, a second section 58, and a third section 60. The third section 60 has a larger diameter than the second section 58, and the second section 58 has a larger diameter than the first section 56. At the interface between the second section 58 and the third section 60, a first ledge 62 is formed, and at the interface between the second section 58 and the first section 56, a second ledge 64 is formed. Additionally, the second sleeve 34 has a ramped protuberance 66 on an inner surface of the second sleeve 34. As shown in FIG. 2, the ramped protuberance 66 may begin proximate the ledge 62 and advance towards the second end 50 of the second sleeve 34 wherein it forms a flange 67. The ramped protuberance 66 may also have a shorter construction as shown in FIG. 1. In a preferred embodiment, a plurality of ramped protuberances 66 are utilized and in a most preferred embodiment, four ramped protuberances 66 are spaced around the inner surface of the second sleeve 34. When a semi-resilient disk, in the form of a hub on the piercing assembly 26, as explained below, moves past the ramped protuberance 66, the semi-resilient disk cannot return past the flanges 67. The third section 60 of the second sleeve 34 further has a hub stop surface 69 that maintains the piercing assembly 26 at an initial first position before the device 10 is placed in the activated position. As further shown in FIG. 1, the second sleeve 34 has a plurality of projections 73. The projections 73 are tapered and designed to abut against the hub of the piercing assembly 26 when the device 10 is in the inactivated position. This prevents the piercing assembly from rattling during shipment and maintains the piercing assembly 26 and sealing member 84 in spaced relation in the inactivated position. As explained in greater detail below, the piercing assembly 26 will move past the projections 73 when the device is moved from the inactivated position to the activated position.

As further shown in FIGS. 1 and 2, the piercing assembly 26 generally comprises the hub 70 which supports a piercing member 76. The piercing member 76 has a first end 78 that is positioned to pass through the opening 46 of the guide 44 of the first sleeve 32 upon activation. A second end 80 of the piercing member 76 is positioned adjacent the gripper assembly 28 when in the inactivated position. The piercing member 76, such as a cannula or needle, is a rigid, elongate, spiked member at each end 78,80 having a central fluid passage 82 for establishing a fluid flow passage between the first container 12 and the second container 14. The piercing member is positioned outside the sidewalls of the first container 12. Each end 78,80 of the piercing member 76 terminates in a sharp point or an oblique angle or bevel adapted to pierce through closures as will be described below. Alternatively, the piercing member 76 can have other end configurations known in the art. In a preferred embodiment, the piercing member 76 comprises a plastic spike 81 at the end 78 and a metal cannula 83 at the end 80. The spike 81 can be integrally molded with the hub 70. The metal cannula 83 preferably fits within the spike 81. The plastic spike 81 is positioned to pierce into the port 16 of the flexible container 12. The metal cannula 83 is positioned to pierce the vial 14. The piercing assembly 26 further has a plurality of wings 75 that extend along the piercing member 76. The wings 75 act as guides to assure the plastic spike 81 is properly aligned to pass through the opening 46 of the guide 44 on the first sleeve 32. In a preferred embodiment, four wings 75 are spaced around the piercing member 76. The hub 70 further has a top surface 71.

As further shown in FIGS. 1 and 2, the hub 70, connected to the piercing member 76, is slideable within the central passageway 35 along an inner surface of the second sleeve 34. In a preferred form of the invention, the hub 70 is generally round or disk-shaped. Preferably, the hub 70 has a greater diameter than the diameter of the second section 58 of the central passageway 35 but a slightly smaller diameter than the third section 60. When activating, the piercing member 76 is allowed to move and pierce the stopper 20 of the drug vial 14 and a sealing member 84 (described below) adjacent the second container 14 when the connector 10 moves from the inactivated position to the activated position. The hub 70 has a stop surface 86 that cooperates with the stop surface 74 of the first sleeve 32. When the device 10 is in the inactivated position, the stop surface 86 cooperates with the ledge 62 (FIGS. 2 and 4) on the second sleeve 34, and the top surface 71 of the hub 70 cooperates with the hub stop surface 69, which keeps the piercing assembly 26 in a first position. The hub 70 further has an annular outer surface 88 that slides along the inner surface of the second sleeve 34 and specifically along the ramped protrusions 66. FIGS. 1 and 2 further show the gripper assembly 28 attached to the second sleeve 34. As discussed, in the preferred embodiment, the gripper assembly 28 is integrally attached to the second end 50 of the second sleeve 34. The gripper assembly 28 generally includes a wall portion 90, a base 91, a finger assembly 92 and a sealing member 84. The gripper assembly 28 serves as an attaching member that is adapted to attach the device 10 to the second container or drug vial 14. The gripper assembly 28 has a central opening 96. The wall portion 90 is preferably annular and forms a cup-like shape in cooperation with the base 91. The wall portion 90 is preferably continuous and solid.

Referring again to FIGS. 1 and 2, the wall portion 90 supports means for fixedly attaching the second container or drug vial 14 to the gripper assembly 28. The means shown are a plurality of segmented fingers that cooperatively form the finger assembly 92. The finger assembly 92 comprises a plurality of alternating segmented fingers 98*a*,98*b* that are connected at their bottom portions. The wall portion 90 has a ledge 97. The bottom portions of the fingers 98 have corresponding structure to the ledge 97. The finger assembly 92 is bonded to the wall portion 90 proximal this area.

The fingers 98*a* are spaced inwardly from the wall portion 90 to allow the fingers 98*a* to flex when a drug vial 14 is inserted into the gripper assembly 28. The fingers 98*b* have a rear portion contacting the wall portion 90 and generally do not flex as will be described in greater detail below. The fingers 98*a*,98*b* are generally trapezoidal in shape and are separated by gaps to define a vial receiving chamber that corresponds to the central opening 96 of the gripper assembly 28 for receiving a top of the vial 14. Though the present device utilizes six fingers 98*a*, 98*b*, it can be appreciated by one of ordinary skill in the art that more or fewer fingers could be utilized without departing from the scope of the present invention. For example, eight fingers could be used.

What is meant by "fixedly attached" is that in order to remove the vial 14 from the connector 10, one would have to exert a force considerably in excess of that normally used to operate the device 10. Such a force likely would break, detach or noticeably deform one or more of the segmented fingers 98 or other portions of the connector 10 in the process.

As further shown in FIG. 1, three of the fingers 98*a* include radially inwardly tapering resilient tabs 104, from a distal end to a proximal end, past which the medical professional must urge a neck of the drug vial 14 in order to connect it to the gripper assembly 28. The tabs 104 are configured such that a space 105 is maintained between the tab 104 and the finger 98*a*. It is appreciated that the tabs 104 are capable of flexing to accommodate varying diameter vial closures. Preferably, the distal end of the fingers 98 have a radiused end that is smooth to avoid cutting the medical personnel handling the connector 10. The tabs 104 could also be formed, however, as solid bumps without departing from the invention.

As also shown in FIG. 1, the remaining fingers 98*b* (one shown) have axially extending, standing ribs 106 extending along an inner surface of the fingers 98*b*. The standing ribs 106 extend proximate a bottom portion of the finger but do not contact the base 91 of the gripper assembly 28. The ribs 106 are spaced from the base by the sealing member 84. In a preferred form, the standing ribs 106 assist in aligning the vial 14 with the vial receiving chamber during insertion. The standing ribs 106 are capable of indenting one or more sidewall portions of the metal crimp ring 22 of the vial 14 in order to inhibit the vial 14 from rotating. While one standing rib 106 is shown on each finger 98*b*, a pair of standing ribs 106 on each finger 98*b* could also be utilized to enhance the prevention of rotation of the vial 14. The fingers 98*b* have a post 107 on a rear portion that contacts the wall portion 90. Thus, when the vial 14 is inserted into the gripper assembly 28, the fingers 98*b* flex very little, if any, while the fingers 98*a* do flex as the fingers 98*a* are spaced inward from the wall portion 90. It is desirable for the fingers 98*b* not to flex in order to maximize the ability of the standing ribs 106 to indent the side of the crimp ring 22 and prevent rotation of the vial 14.

As further shown in FIG. 1, the fingers 98*b* having the standing ribs 106 are slightly taller than the fingers 98*a* with the tabs 104. The fingers 98*b* have a flat lead-in section 99. The flat lead-in section 99 helps to properly align the vial 14 as it is inserted into the gripper assembly 28. Because the fingers 98*b* are taller than the fingers 98*a*, the vial 14 is aligned by the lead-in sections 99 and then contacts the tabs 104 as the vial 14 is further inserted into the gripper assembly 28.

While three fingers 98*a* with resilient tabs 104 and three fingers 98*b* with standing ribs 106 is preferred, providing more or fewer fingers with resilient tabs 104 or standing ribs 106 would not depart from the scope of the invention. It is also preferable that the fingers 98*a* with the tabs 104 and the fingers 98*b* with the standing ribs 106 are disposed in alternating order. It may also be desirable to place a flexible restraining member, such as shrink wrap or the like, around the fingers 98*a*,98*b* to assist in gripping the vial 14.

The wall portion 90 further has a first annular rim 108 extending from the base 91. The finger assembly 92 has a bottom portion 93 having a second annular rim 110 extending therefrom and towards the first annular rim 108. The second annular rim 110 is coradial with the first annular rim 103 and is longitudinally displaced therefrom. The rims 108,110 cooperate with the sealing member 84 to be described in greater detail below. The finger assembly 92 is ultrasonically welded to the inner surface of the wall portion 90. In this manner, the sealing member 84 is positioned between the base 91 of the wall portion 90 and the bottom portion 93 of the finger assembly 92 wherein the sealing member 84 hermetically seals the central passageway 35 and the piercing member 26 disposed therein.

Figure 5:
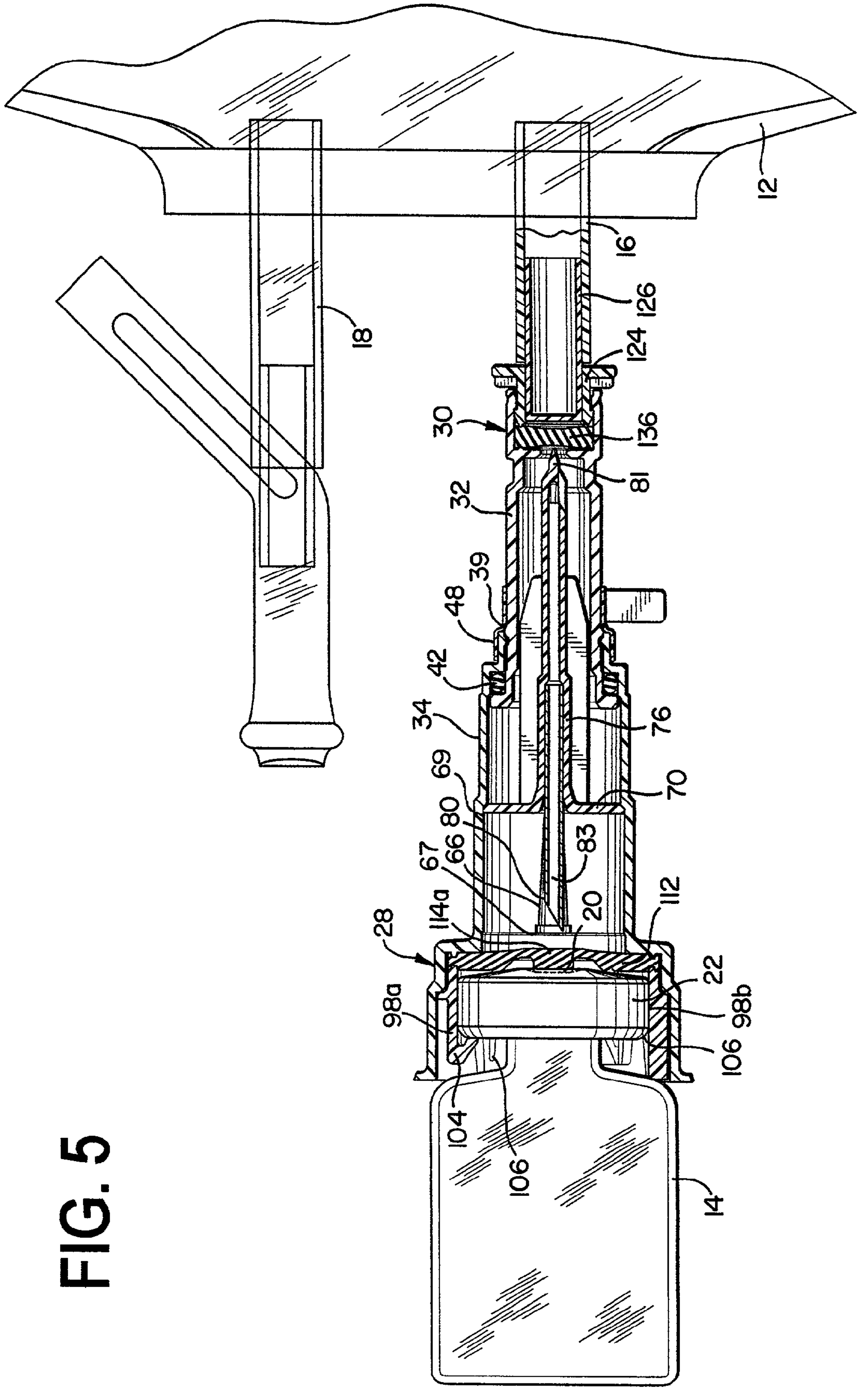
FIG. 5 is a cross-sectional view of the connector device of the present invention having a drug vial fixedly secured to the connector device, the connector device being in an inactivated position.

As further shown in FIGS. 1 and 2, the sealing member 84, sometimes referred to as a septum 84, is positioned within the gripper assembly 28. In a preferred embodiment, the sealing member 84 has a base 111 and an annular ridge 112. The base has first and second surfaces. The base is preferably disk-shaped. The annular ridge 112 extends axially from the disk and towards the top of the vial 14. The annular ridge 112 is dimensioned to tightly and sealingly fit over the rubber stopper 20 of the vial 14 to prevent leakage from the vial 14. In a preferred embodiment, the annular ridge 112 tapers axially-outwardly. In addition, the annular ridge 112 of the sealing member 84 is capable of deforming to accommodate dimensional variations in a height of a closure of the second container. The sealing member 84 can be pre-slit at a central location corresponding to the end 80 of the piercing member 76. In one preferred embodiment, the sealing member 84 has a center hub 114 having a thickened cross-section as shown in FIG. 1. The center hub 114 is positioned to be pierced by the piercing member 76 during activation of the device 10. In one preferred embodiment, the piercing member 76 is buried into the thickened center hub 114, without passing through the hub 114, as the plastic spike 83 pierces into the container 12. FIG. 5 shows the sealing member 84 having a thickened center hub 114*a* that is slightly thinner than the center hub 114 shown in FIG.

1. The disk-shaped sealing member 84 has a web 85 of thinner cross-section than the center hub 114. The web 85 assists the hub 114 in flexing to accommodate dimensional variations in the vial 14. The annular ridge 112 is positioned circumjacent the center hub 114 and the web 85. A first annular groove 113 is positioned at an outer periphery of the sealing member 84 on a first side of the sealing member 84. A second annular groove 115 is positioned on a second side of the sealing member 84 generally opposite annular groove 115. When the device is assembled, the first annular groove 113 receives the first annular rim 108 and the second annular groove 115 receives the second annular rim 110 wherein the sealing member 84 is sandwiched between the base 91 and the bottom portion 93 of the finger assembly 92. In this configuration, the sealing member 84 hermetically seals the passageway 35 and sealing member 76 at the second end 50 of the second sleeve 34. In one form, the sealing member 84 can be sized slightly larger such that when the annular grooves 113,115 receive the annular rims 108,110, the sealing member 84 is subjected to a radial compressive force. This assists the sealing member 84 is accounting for dimensional variations of vials 14 that are inserted into the gripper assembly 28. Also, the sealing member 84 can be lubricated, which lubricates the piercing member 76 allowing it to enter the drug vial 14 more easily. The sealing member 84 is preferably made from silicone rubber.

In an alternative embodiment, the sealing member 84 could have a central opening. The central opening receives the piercing member 76 when the connector 10 is moved from its inactivated position to the activated position. The central opening would also allow for steam sterilization past the sealing member 84.

As also shown in FIGS. 1 and 2, the wall portion 90 has a lip 122 at its outer periphery. An end cap, or flip cap 124 is dimensioned to snap over the lip 122 to seal the gripper assembly 28 before a vial 14 is inserted into the gripper assembly 28. No orientation of the end cap 124 is required. The lip 122 is preferably integrally molded with the wall portion 90. The end cap 124 is preferably made from plastic or other suitable material. The end cap 124 provides a hermetic seal between the exterior of the device 10 and the central opening 96. A tape strip (not shown) could be stretched across the end cap 124 and attached to outer surfaces of the wall portion 90 as a tamper evident feature.

Alternatively, a seal material can be releasably secured to the wall portion 90 such as by heat sealing wherein the material can be peeled away by pulling a tab formed on the seal material. The wall portion 90 provides for a solid surface to mount the seal material therefore hermetically sealing the connector 10. The seal material can be made of aluminum foil, or of polymeric based material such as TYVEK®, and more preferably TYVEK® grade 1073B, or spun paper or other material that is capable of being peelably attached to the wall portion 90 and capable of providing a barrier to the ingress of contaminants. It is also contemplated that sealing can be accomplished through induction welding or other sealing techniques.

FIGS. 1–3 show the port connector 30 of the device 10. The port connector 30 serves as a first attaching member to connect the first container 12 to the device 10. The port connector 30 includes a first attaching element 124 generally in the form of a port snap 124 and a second attaching element 126 generally in the form of a container sleeve 126. The container sleeve 126 is generally cylindrical and has one end closed by a membrane 128. The port snap 124 is also generally cylindrical and dimensioned to receive the container sleeve 126. The port snap 124 has a flange 130 extending around its outer surface. A distal end of the port snap 124 has a generally circular, tapered finger 132 extending therefrom.

The container sleeve 126 is inserted into the port snap 124 and connected thereto preferably by solvent bonding an outer surface of the sleeve 126 to an inner surface of the port snap 124, thus forming the port connector assembly 30. The membrane 128 of the sleeve 126 is positioned at the flange end of the port snap 124. As shown in FIGS. 1–3, before connecting the port connector assembly 30 to the second end 36 of the first sleeve 32, a second sealing member 136, preferably in the form of a rubber septum, is inserted into the second end 36 of the first sleeve 32. The second sealing member 136 is positioned adjacent the guide 44 wherein the projection 47 indents the second sealing member 136. If desired, the second sealing member 136 could be pre-slit. The second sealing member 136 prevents "drip-back" after the deactivation procedure as will be described in greater detail below. The port snap 124 is then inserted and urged into the first sleeve 32 wherein the flange 130 passes by the protrusion 49 of the first sleeve 32. The resiliency of the materials allow the flange 130 to snap back after passing by the protrusion 49 wherein a tight interference fit is formed between the port connector 30 and the first sleeve 32. Once inserted, the tapered finger 132 indents the second sealing member 136, thus sandwiching the second sealing member 136 between the guide 44 and the port snap 124.

As shown in FIG. 4, the port connector assembly 30 is also connected to the first container 12 wherein the outer surface of the container sleeve 126 is connected to an inside surface of the container port 16. In a preferred embodiment, this connection is performed using an electron-beam process as disclosed in commonly-assigned U.S. patent application Ser. No. 09/294,964 entitled "Method and Apparatus For Manipulating Pre-Sterilized Components In An Active Sterile Field," which is expressly incorporated herein by reference. Other methods of connection are also possible such as solvent bonding.

It is understood that in a preferred embodiment, the protrusion 49 and flange 130 are formed around a full periphery of the first sleeve 32 and port snap 124 respectively. These structures can also be in the form of an interrupted annular ridge, a plurality of bumps or even a single bump.

Typically, the connector 10 is connected to the flexible bag 12 prior to shipping. It will be appreciated by one of ordinary skill in the art, however, that the connector 10 could be connected to the first container 12 at different times.

Referring to FIG. 1, the device 10 can optionally include a tamper-evident strip 150, which is preferably made from adhesive material. The tamper-evident strip 150 can be attached at a juncture between the first sleeve 32 and the second sleeve 34 and over the detent 39. Medical personnel must remove the strip 150 in order for the first sleeve 32 and the second sleeve 34 to be capable of relative axial movement. Optionally, the tamper evident strip 150 could be capable of indicating the first and second sleeves 32,34 have been moved axially with respect to one another, rather than preventing such movement, by becoming damaged upon such movement. The tamper-evident strip 150 can also include a flap 152 for removing the tamper evident strip 150. In this manner, the tamper evident strip 150 can indicate to a medical professional that someone has used or tampered with the device 10 by the fact that the tamper evident strip 150 is missing or damaged. The tamper evident strip 150 can take alternative forms as shown in FIG. 21.

FIGS. 1, 2 and 4 show the connector 10 in its inactivated position where the connector 10 is in its most elongated state. In this inactivated position, the stop surface 51 of the first sleeve 32 abuts the stop surface 64 of the second sleeve 34. The hub 70 is maintained between the hub stop surface 69 and the ledge 62. FIGS. 4–7 disclose the activation process for the connector 10. FIG. 4 shows the device 10 connected to the flexible container 12. As shown in FIG. 5, the end cap 124 is first flipped off the gripper assembly 28. The vial 14 is then inserted into the gripper assembly 28 wherein the fingers 98*a* flex towards the wall portion 90 until the vial 14 passes by the tabs 104 wherein the neck of the vial 14 is positioned between the tabs 104 and the sealing member 84. The standing ribs 106 on the fingers 98*b* indent a side portion of the crimp ring 22 on the vial 14. Thus, the vial 14 is fixedly attached to the connector 10. As further shown in FIG. 5, the annular ridge 112 of the sealing member 84 forms a fluid tight seal over the top of the vial 14. Thus, a vial 14 can be selectively docked to the connector 10 without piercing the stopper 20 of the vial 14. As further shown in FIG. 5, the second end 80 of the piercing member 76 is positioned close to the center hub 114 of the sealing member 84. This reduces the stroke length or distance the piercing member 76 must travel to pierce the sealing member 84 and the stopper 20 of the drug vial 14.

Figure 6:
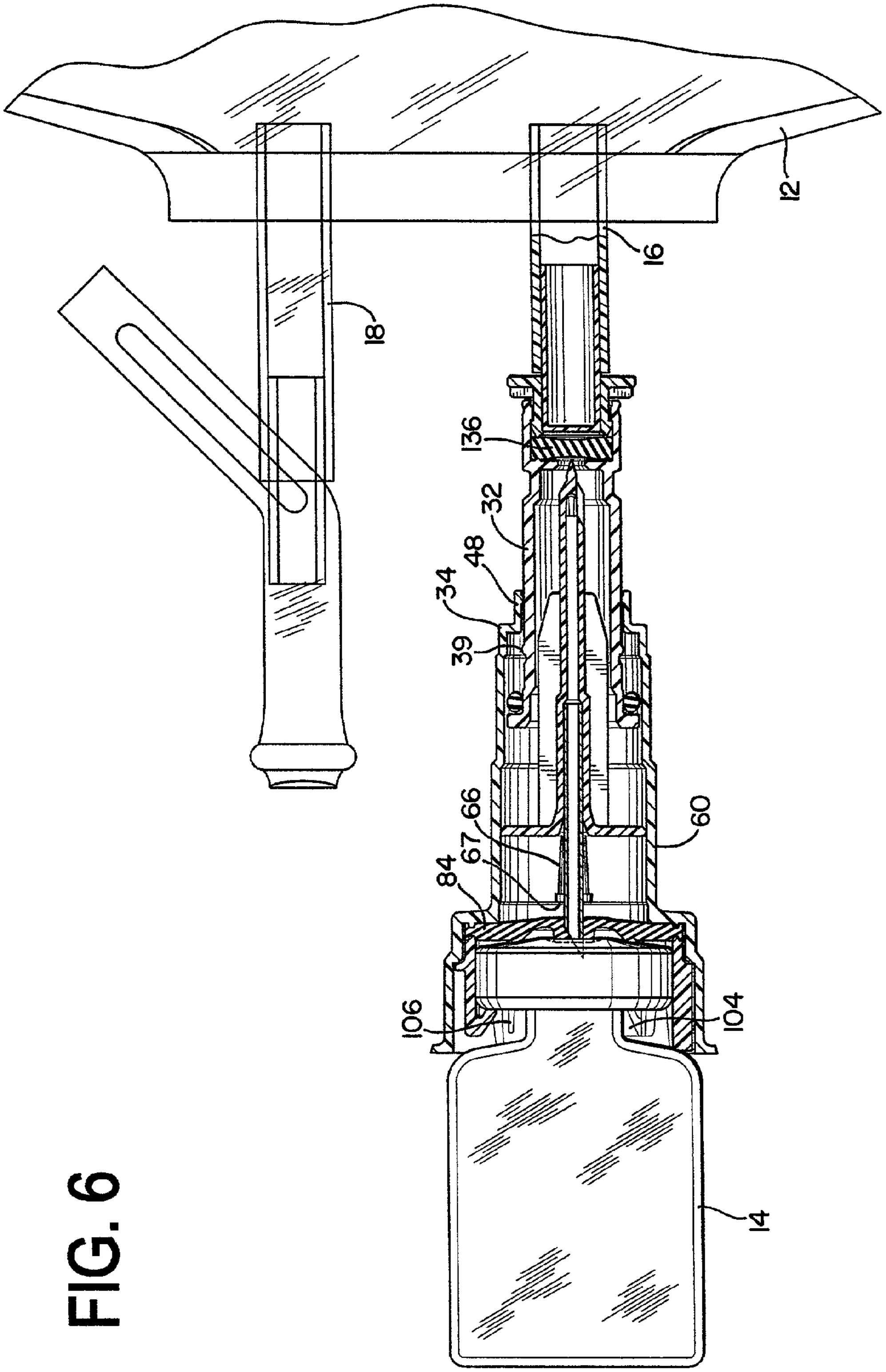
FIG. 6 is a cross-sectional view of the connector device shown in FIG. 5 wherein the connector device is in the initial stages of an activation process.

FIG. 6 shows the connector device 10 as the activation process commences. To activate, the tamper-evident strip 150 is first peeled away from the sleeves 32,34. The vial 14 in the gripper assembly 28, along with the second sleeve 34, are moved axially towards the flexible container 12. Adequate force must be applied so that the first end 48 of the second sleeve 34 moves past the detent 39 on the first sleeve 32. As the second sleeve 34 moves along the first sleeve 32, the plastic spike 81 will engage the second sealing member 136. Because of the materials used, the plastic spike 81 will not yet pierce through the second sealing member 136. The friction associated with this engagement will cause the hub 70 to move along the second sleeve 34 wherein the metal cannula 83 will pierce the sealing member 84 and closure of the vial 14. As shown in FIG. 7, as the second sleeve 34 further moves along the first sleeve 32, the stop surface 74 on the first sleeve 32 moves towards and engages the stop surface 86 of the hub 70 on the piercing assembly 76. The hub 70 thus moves along the third section 60 of the second sleeve 34 wherein the hub 70 rides along the ramped protuberances 66 and eventually passes over the flanges 67. This movement forces the metal cannula 83 at the second end 80 of the piercing assembly 76 to pierce completely through the center hub 114 and stopper 22 and thus into the vial 14. The second end 80 of the piercing member 76 now experiences greater friction as it penetrates the stopper 22 of the vial 14. This friction causes the plastic spike 81 at the first end 78 of the piercing member 76 to advance towards the flexible container 12. The plastic spike 81 pierces through the second sealing member 136 and the membrane 128.

As also shown in FIG. 7, the sleeves 32, 34 translate axially wherein the hub 70 advances to against the sealing member 84; also, the first end 48 of the second sleeve 34 proceeds to the first end 36 of the first sleeve 32. This position (FIG. 7) represents the activated position. In the activated position, the metal cannula 83 at the second end 80 of the piercing member 76 is pierced through the stopper 20 of the vial 14, and the plastic spike 81 at the first end 78 of the piercing member 76 is pierced through the second sealing member 136. Thus, fluid communication is established between the flexible bag 12 and the vial 14 through the central fluid passageway 82 of the piercing member 76.

It is understood that when the connector 10 is in the inactivated position, the central passageway 35 is sealed in a substantially air-tight fashion at one end by the sealing member 84, at an opposite end by the second sealing member 136 and at the interface between the sleeves 32,34 by the sealing member 42. As the vial 14 and second sleeve 34 advance towards the flexible container 12 during the activation process, the volume of the central passageway 35 necessarily decreases thus pressurizing the air located in the central passageway 35. This pressurized air must be relieved before the connector 10 reaches the final activated position. Accordingly, when the o-ring 42 moves past the first section 56 of the second sleeve 34 to the larger diameter of the second section 58 of the second sleeve 34, the sealing member 42 no longer contacts the inner surface of the second sleeve 34 (FIG. 6) thus allowing the pressurized air to be relieved through the junction of the sleeves 32,34.

In the activated position shown in FIG. 7, the diluent contained in the flexible container 12 can pass through the piercing member 76 to reconstitute the drug contained in the vial 14. Once the drug is reconstituted and the resulting mixture passes completely through the piercing member 76 and into the flexible container 12, the drug vial 14 and second sleeve 34 can be pulled back away from the flexible container 12. As shown in FIG. 8, when the second sleeve 34 is pulled back, the piercing assembly 26 is retained in position by the flange 67 of the ramped protuberance 66. The stop surface 74 of the first sleeve 32, however, does not contact the ramped protuberance 66 and can be retracted. The metal cannula 83 of the piercing member 76 remains in the closure of the vial 14 and the plastic spike 81 of the piercing member 76 is pulled past the membrane 128 and the second sealing member 136 (FIG. 8). This position is referred to as the deactivated position, or post reconstitution position. The second sealing member 136 is resilient and forms a seal once the plastic spike 81 passes by, thus preventing any of the resulting mixture from dripping back into the drug vial 14 or passing into the passageway 35 of the sleeve assembly 24.

The resulting mixture can then be delivered to a patient through appropriate tubing sets (not shown) attached to the second port 18 on the flexible container 12.

Figure 9:
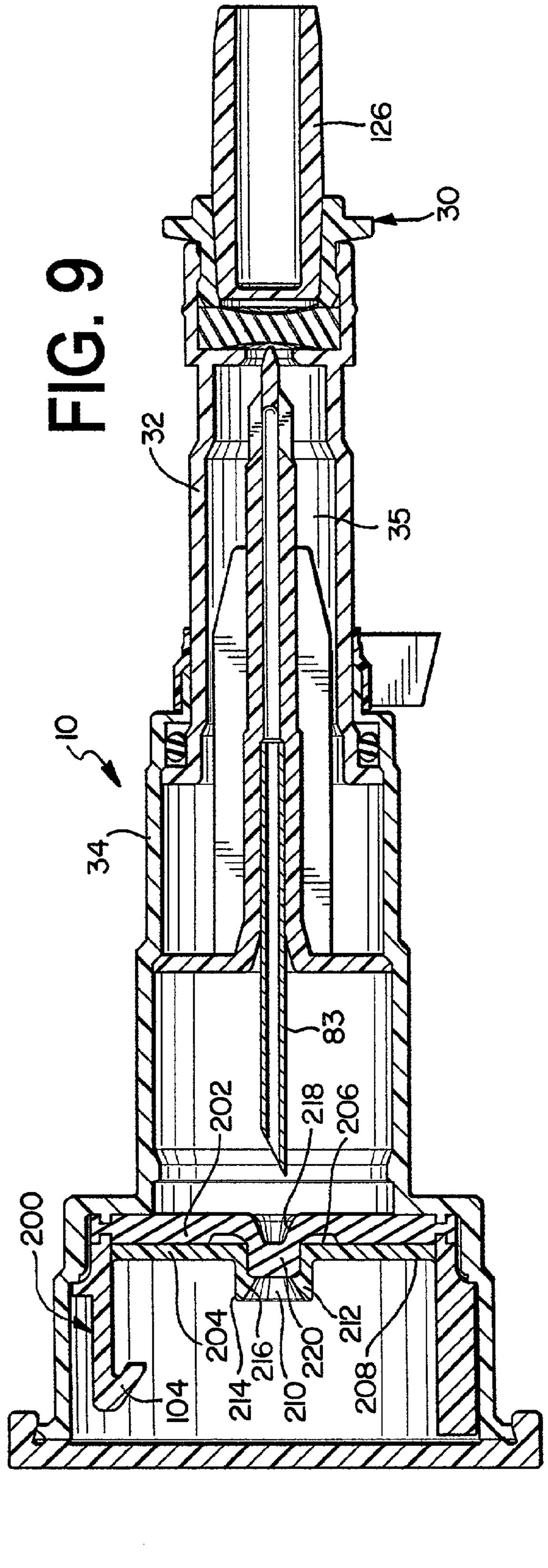
FIG. 9 is a cross-sectional elevation view of the connector device of the present invention having an alternative vial connecting device and sealing member.
Figure 10:
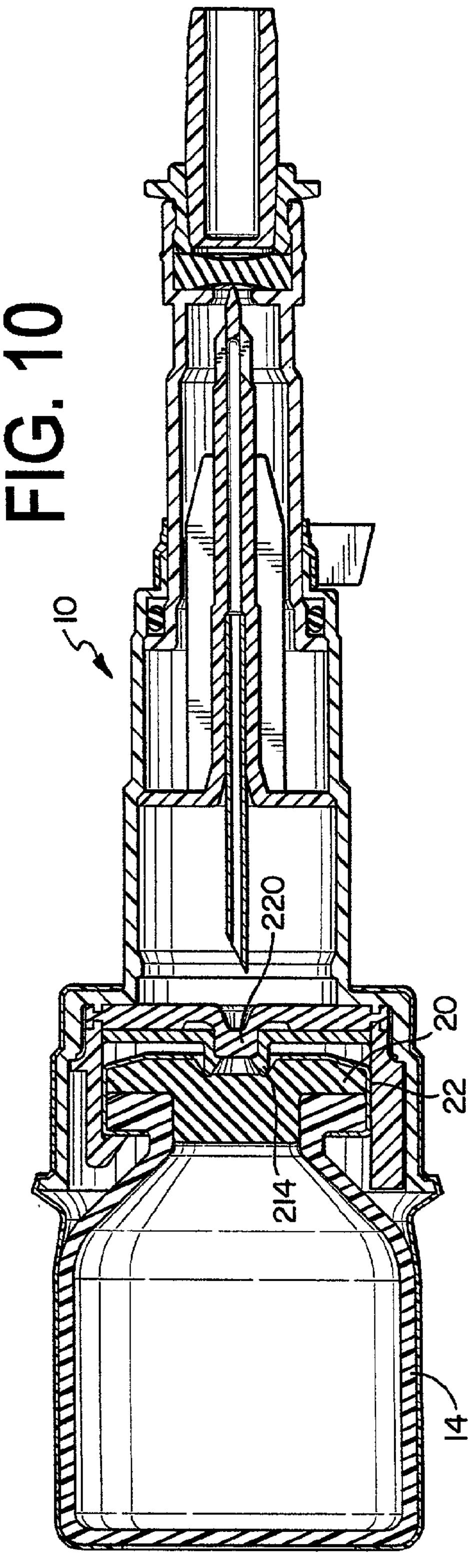
FIG. 10 is a cross-sectional view of the connector device shown in FIG. 9 having a drug vial fixedly secured to the connector device, the connector device being in an inactivated position.

FIGS. 9 and 10 disclose another embodiment of the connector device 10 having an alternative vial connecting structure. Similar elements will be designated with the same reference numerals. As shown in FIG. 9, the connector device 10 utilizes an alternative finger assembly 92, generally designated with the reference numeral 200, as well as an alternative sealing member 84, or septum, generally designated with the reference numeral 202. The finger assembly 200 has a disk-shaped base or panel 204 at a bottom portion of the fingers 98. The panel 204 has a first side 206 and a second side 208. The panel 204 further has a center opening 210 extending through the panel 204 from the first side 206 to the second side 208. The panel 204 also has an annular ring 212 extending from the second side 208 of the disk. The annular ring 212 has a rounded end surface 214 that is generally blunt. The annular ring 212 further has an inner lip 216. The panel 204 and annular ring 212 are preferably integrally molded with the finger assembly 92 of a rigid material. In a most preferred embodiment, the annular ring 212 is made from PVC material. The septum 202 is similar to the septum 84 but has a conical-shaped central portion 218 that supports a center plug 220. The septum 202 is supported in the connector device 10 similar the previously-described septum 84. The septum 202 is positioned between the base 91 and a bottom portion of the finger assembly 92 wherein the panel 204 extends over the septum 202. The center plug 220 fits into the center opening 210 and abuts against the inner lip 216.

FIG. 10 shows the connector device 10 having the vial 14 fixedly secured to the gripper assembly 28. As previously discussed, the vial 14 has a crimp ring 22 that has an aperture or circular opening on the rubber stopper 20 that plugs the opening of the vial 14. The opening defines a target site of the rubber stopper 20. As shown in FIG. 10, the annular ring 212 is sized such that it fits within the opening of the crimp ring 22. The annular ring 212 does not contact the crimp ring 22. As discussed, the annular ring 212 is rigid and has a hardness greater than the rubber stopper 20. The annular ring 212 deforms the rubber stopper 20 but does not cut or pierce into the stopper 20. The annular ring 212 sealingly engages the rubber stopper 20 to form a fluid tight seal against the closure member or stopper 20. Once sealed, the metal cannula 83 pierces through the center plug 220 passing through the annular ring 212 and stopper 20 and into the vial 14. In a preferred embodiment, the annular ring 212 is integrally connected to the panel 204 and finger assembly 92. Alternatively, the septum 202 could be modified to support the rigid annular ring 212.

Figure 11:
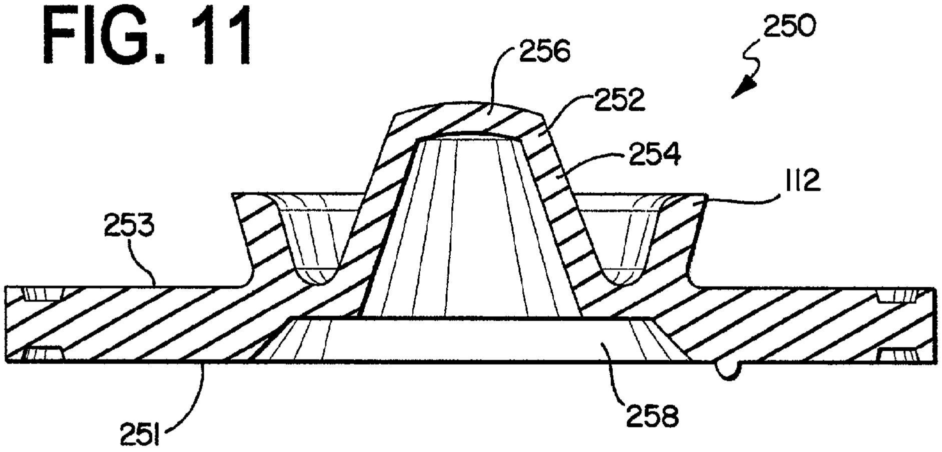
FIG. 11 is a cross-sectional view of an alternative embodiment of the sealing member used in the connector device.
Figure 12:
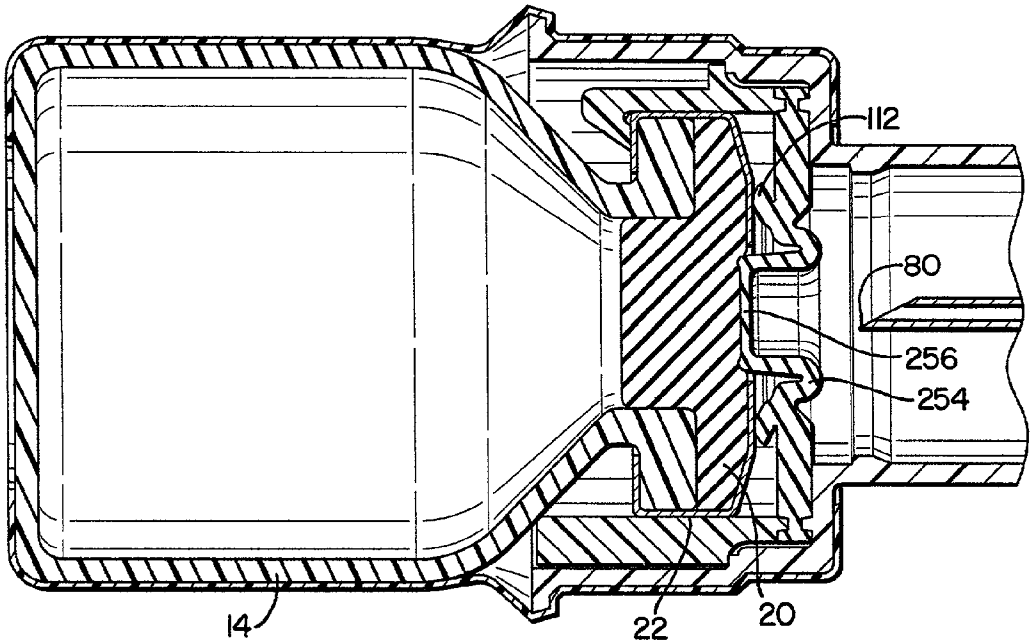
FIG. 12 is a cross-sectional view of the connector device of the present invention utilizing the sealing member of FIG. 11 and having a drug vial fixedly secured to the connector device, the connector device being in an inactivated position.

FIGS. 11 and 12 disclose another embodiment of the sealing member 84, used with the connector device 10, generally designated by the reference numeral 250. Similar elements will be referred to with identical reference numerals. Similar to the sealing member 84 discussed above, the sealing member 250 has a disk-shaped base having a first surface 251 and a second surface 253. The annular ridge 112 extends axially from the second surface 253 of the disk and towards the top of the vial 14. The sealing member 250 further has a cap 252 concentrically disposed within the annular ridge 112 and that also extends from the second surface 253 of the disk. The cap 252 is generally in the form of a conical frustum. The cap 252 has a frustoconical sidewall 254 connected to a top wall 256. In a preferred embodiment, the top wall 256 has a slight concave shape. The frustoconical sidewall 254 extends from the disk towards the vial 14 further than the annular ridge 112. The sealing member 250 has a recessed portion 258 on an underside surface adjacent to a bottom portion of the sidewall 254.

FIG. 12 discloses the sealing member 250 connected in the connector device 10 similar to the sealing member 84 as well as a vial 14 connected to the gripper assembly 28. As shown, the top wall 256 of the cap 252 deflects into a generally planar position to tightly and sealingly fit against the rubber stopper 20 of the vial 14. If desired, the rubber stopper 20 could be molded with a depression to accommodate the top wall 256. The frustoconical sidewall 254 bows outwardly. Thus, the cap 252 does not deform the rubber stopper 20. The annular ridge 112 tightly and sealingly fits over the crimp ring 22 of the vial 14. The recessed portion 258 accommodates the deflection of the cap 252 against the vial 14. Thus, the sealing member 250 provides a dual fluid tight seal against the closure member of the vial 14. The cap 252 sealingly fits against the target site of the rubber stopper 20 and the annular ridge 112 sealingly fits against an outer portion of the rubber stopper 20. The sealing member 250 provides even greater sealing capabilities by providing a dual-seal structure. Like the sealing member 84, the sealing member 250 can also be preferably made from Silicone PL-S146.

In both the sealing structures disclosed in FIGS. 9–12, a seal is provided directly against the rubber stopper 20. The annular ring 212 and cap 252 provide a seal against the target site of the rubber stopper 20. In the unlikely event that the rubber stopper became contaminated in an area underneath the crimp ring 22, sterility would not be comprised since the annular ring 212 and cap 252 directly seal against the rubber stopper 20.

FIGS. 13–18 disclose another embodiment of the sealing member 84, used with the connector device 10, generally designated by the reference numeral 300. As shown, the sealing member 300 generally includes a base 302, a diaphragm 304, and an annular ridge 306.

Figure 13:
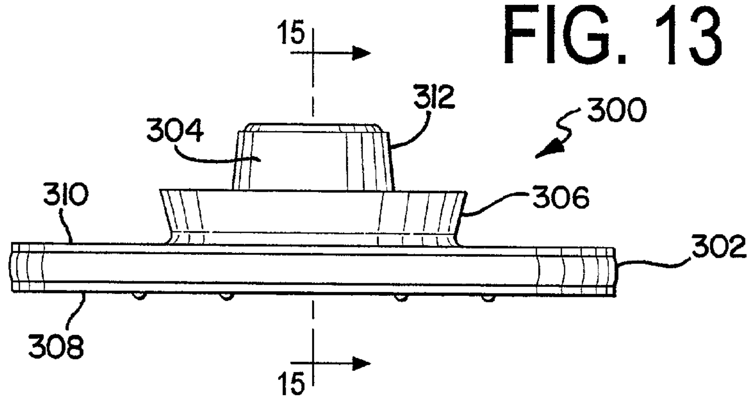
FIG. 13 is a front elevation view of another embodiment of the sealing member used in the connector device of the present invention.
Figure 14:
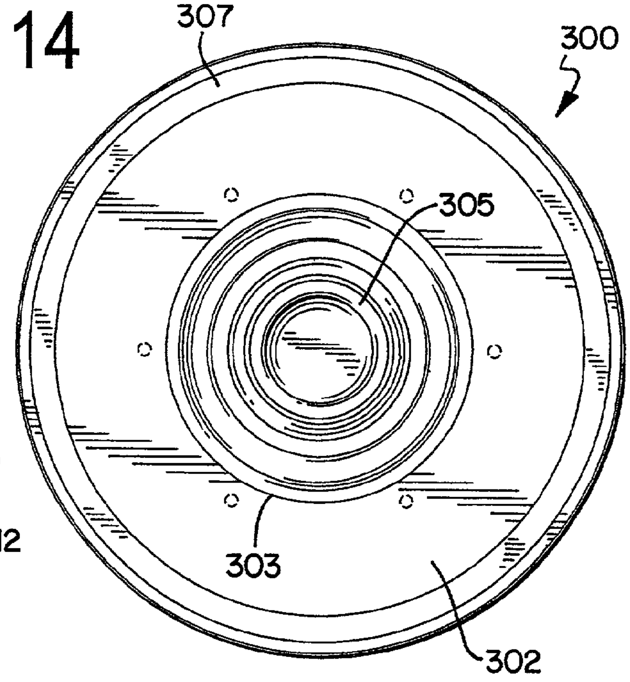
FIG. 14 is a top view of the sealing member of FIG. 13.
Figure 15:
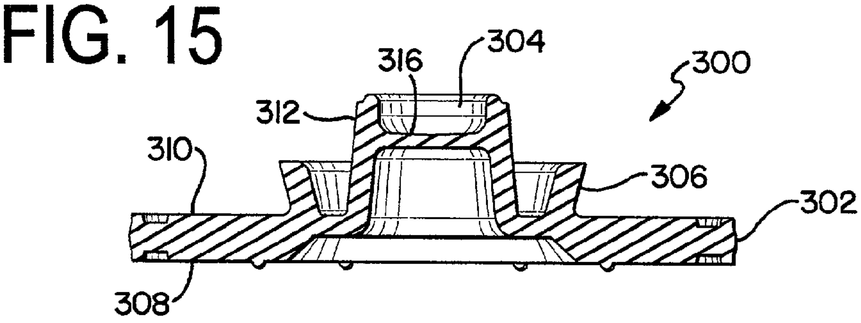
FIG. 15 is a cross-sectional view of the sealing member taken along lines 15—15 in FIG. 13.

As generally shown in FIGS. 13–15, the base 302 is generally disk-shaped. The disk or base 302 has a first surface 308 and a second surface 310. The first surface 308 faces into the connector 10 and the second surface 310 faces the container to be attached to the connector 10. The base 302 has the identical grooved structure at its periphery to attach the sealing member 300 to the connector 10 as described above.

Figure 16:
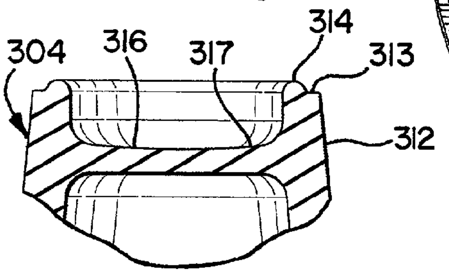
FIG. 16 is a partial cross sectional view of the sealing member shown in FIG. 15.

The diaphragm member 304 is generally a flexible member that extends from the second surface 310 of the base 302. The diaphragm member 304 extends from a generally central portion of the base 302. The diaphragm member 304 may be considered to be frustoconical in shape. The diaphragm member 304 has a frustoconical or annular sidewall 312 and a membrane 316 extending across and connected to the annular sidewall 312. The membrane 316 of the diaphragm member 304 is adapted to confront the closure member of the vial 14. As shown in FIG. 16, the membrane 316 has an outer surface 317 that is preferably slightly convex. The annular wall 312 has a lip 313 extending therefrom. The lip 313 is also annular. At a distal end, the lip 313 has a rounded protrusion 314. As explained in greater detail below, the diaphragm member 304 is capable of forming a first fluid tight seal with the closure of the container.

The annular ridge 306 extends from the second surface 310 of the disk 302. The annular ridge 306 is circumjacent the diaphragm 304 and is positioned outwardly of the diaphragm member 304. The annular ridge 306 tapers axially-outwardly from a proximal end to a distal end. As explained in greater detail below, the annular ridge 306 is capable of forming a second fluid tight seal with the closure of the container. As shown in FIGS. 13 and 15, the diaphragm member 304 extends from the second surface 310 at a first length. The annular ridge 306 extends from the second surface 310 at a second length. The second length is less than the first length, thus, the diaphragm member 304 extends from the second surface 310 a greater distance than the annular ridge 306.

Figure 17:
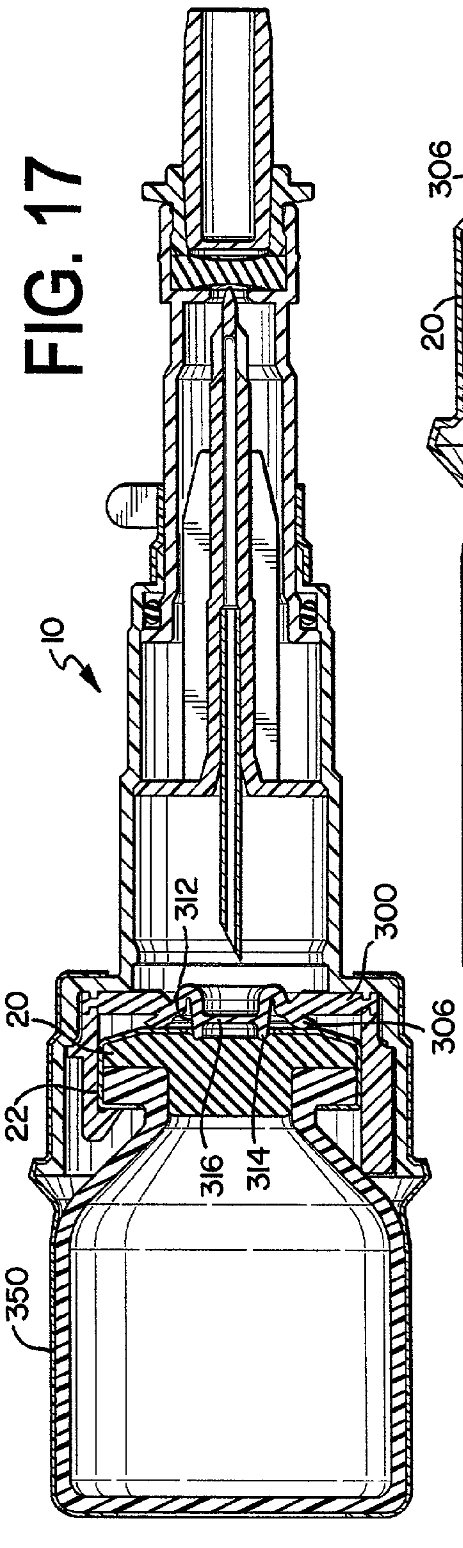
FIG. 17 is a cross-sectional view of the connector device of the present invention utilizing the sealing member of FIG. 13.
Figure 18:
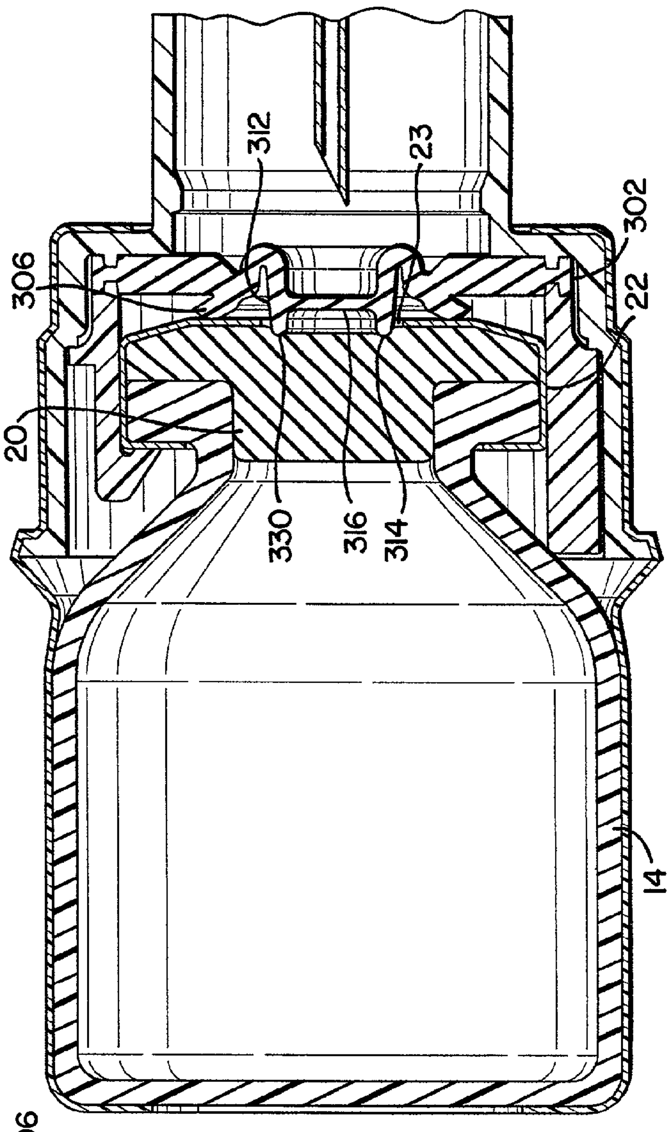
FIG. 18 is an enlarged partial cross-section view showing the sealing member of FIG. 13 sealing a drug vial.

FIGS. 17–18 show the sealing member 300 connected to the connector 10. The sealing member 300 is connected similarly as described above. FIGS. 17–18 also show the vial 14 connected to the connector 10. As discussed above, the vial 14 has a closure member that includes a rubber stopper 20 and a crimp ring 22. The crimp ring 22 has a central opening defining a target sight 23 (FIG. 18) on the rubber stopper 20. It is further noted that the vial 14 may be connected to the connector 10 and then have a shrink wrap member 350 applied over the vial 14 and connected to the gripper assembly 28. The vial 14, connector 10 (inactivated) and container 12 may be shipped in this fashion if desired.

When the vial 14 is connected to the connector 10, the sealing member 300 provides a dual seal on the vial 14. In particular, the diaphragm member 304 abuts the closure to provide a first fluid tight seal with the closure of the vial 14, and the annular ridge 306 abuts the closure to provide a second fluid tight seal with the closure of the vial 14. Specifically, the rounded protrusion 314 of the diaphragm member 304 indents the rubber stopper 20 at the target site 23 to form the first seal. A space 330 is maintained between the crimp ring 22 and the annular wall 312 and membrane 316 of the diaphragm member 304. The membrane 316 confronts the rubber stopper 20. The annular ridge 306 deflects outwardly against the crimp ring 22 to form the second seal. It is understood that other variations are possible to form a dual-seal such as with an o-ring.

As further shown in FIGS. 17 and 18, when the vial 14 is connected to the connector 10, the diaphragm member 304 initially contacts the rubber stopper 20 of the vial 14. As the vial 14 further advances into the gripper assembly 28, the diaphragm member 304 initially is displaced towards the piercing member 76. Upon further advancement, the annular wall 316 folds upon itself while the lip 312 forms a fluid tight seal on the rubber stopper 20. This action also moves the membrane 316 into a second position wherein the surface 317 moves from the slightly convex surface to a generally planar surface. The respective heights and flexibility of the diaphragm member 304 and annular ridge 306 allow these components to account for dimensional differences in heights of different closures.

Figure 19:
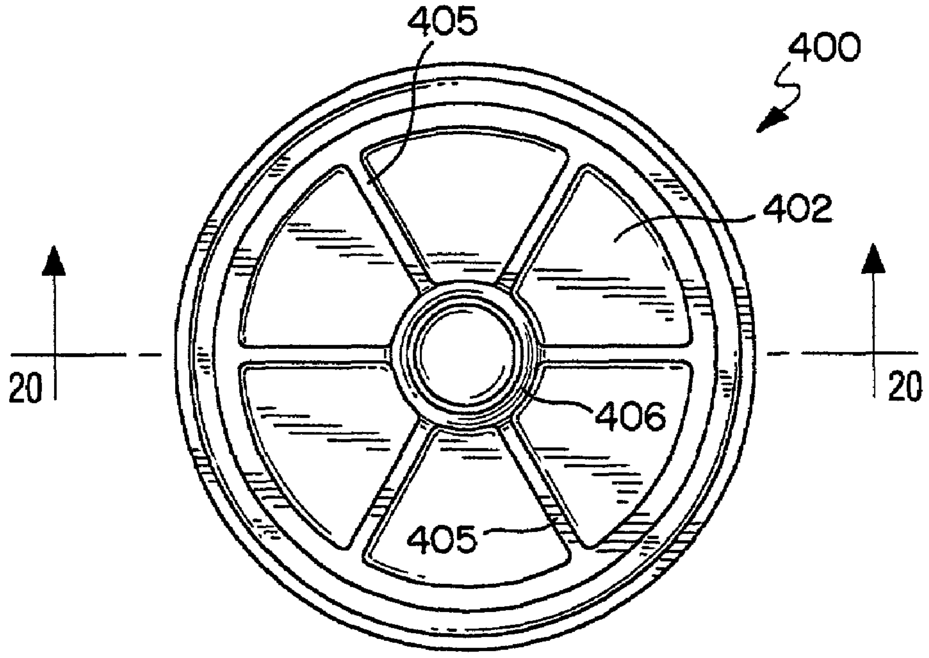
FIG. 19 is a plan view of another embodiment of the sealing member used in the connector device of the present invention.
Figure 20:
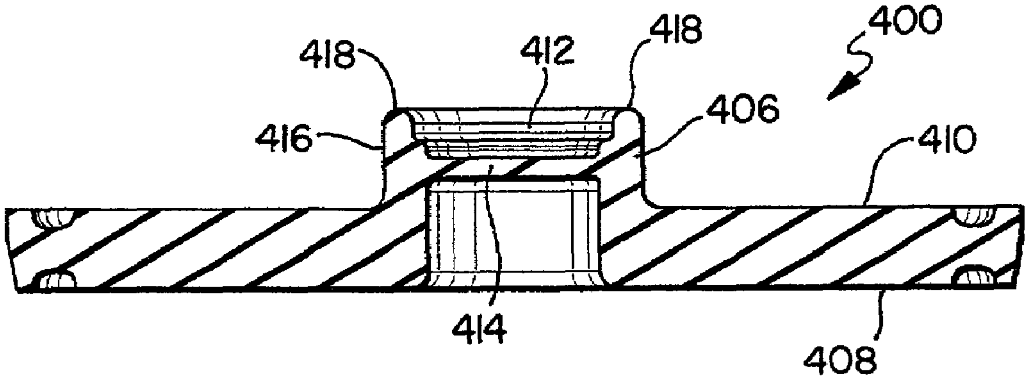
FIG. 20 is a cross-sectional view of the sealing member taken along lines 20—20 in FIG. 19.

FIGS. 19–21 disclose another embodiment of the sealing member 84, used with the connector device 10, generally designated by the reference numeral 400. The sealing member 400, or septum 400, generally has a base 402 and an annular ring 406. The septum 400 is a single integral component made from a generally rigid material. As such, the septum 400 is preferably injection-molded in a single process. In one preferred embodiment, the septum 400 is made from polyethylene. PVC material may also be used.

As generally shown in FIGS. 19 and 20, the base 402 is generally disk-shaped. The disk or base 402 has a first surface 408 and a second surface 410. The first surface 408 faces into the connector 10 and the second surface 410 faces the container to be attached to the connector 10. The base 402 has the identical grooved structure at its periphery to attach the sealing member 400 to the connector 10 as described above. The base 402 also has a plurality of spokes 405 extending from the annular ring 406 along the base 402.

As the annular ring 406 is preferably integrally molded with the base 402, the annular ring 406 is a rigid member. The annular ring 406 extends from the second surface 410 of the base 402. The annular ring 406 is positioned at generally a central portion of the base 402. The ring 406 defines an opening 412, preferably a center opening 412, in the base 402. A membrane 414 is positioned in the center opening 412. In one embodiment, the membrane 414 maybe considered a portion of the base 402 and integrally molded with the base 402. In a preferred embodiment, the membrane 414 is axially spaced from the base 402. This placement provides for enhanced sterilization and helps prevent the piercing member from coring a hole in the membrane 414 wherein the cored portion would block the piercing member 76. The membrane 414 is also designed to be spaced from the closure 20 of the vial 14 when the vial s14 is connected to the connector 10.

The rigid annular ring 406 has a protrusion 416 at a distal end. The protrusion 416 is tapered to a rounded end 418. The rigid annular ring 406 is capable of forming a fluid tight seal with the closure 20 of the vial 14.

Figure 21A:
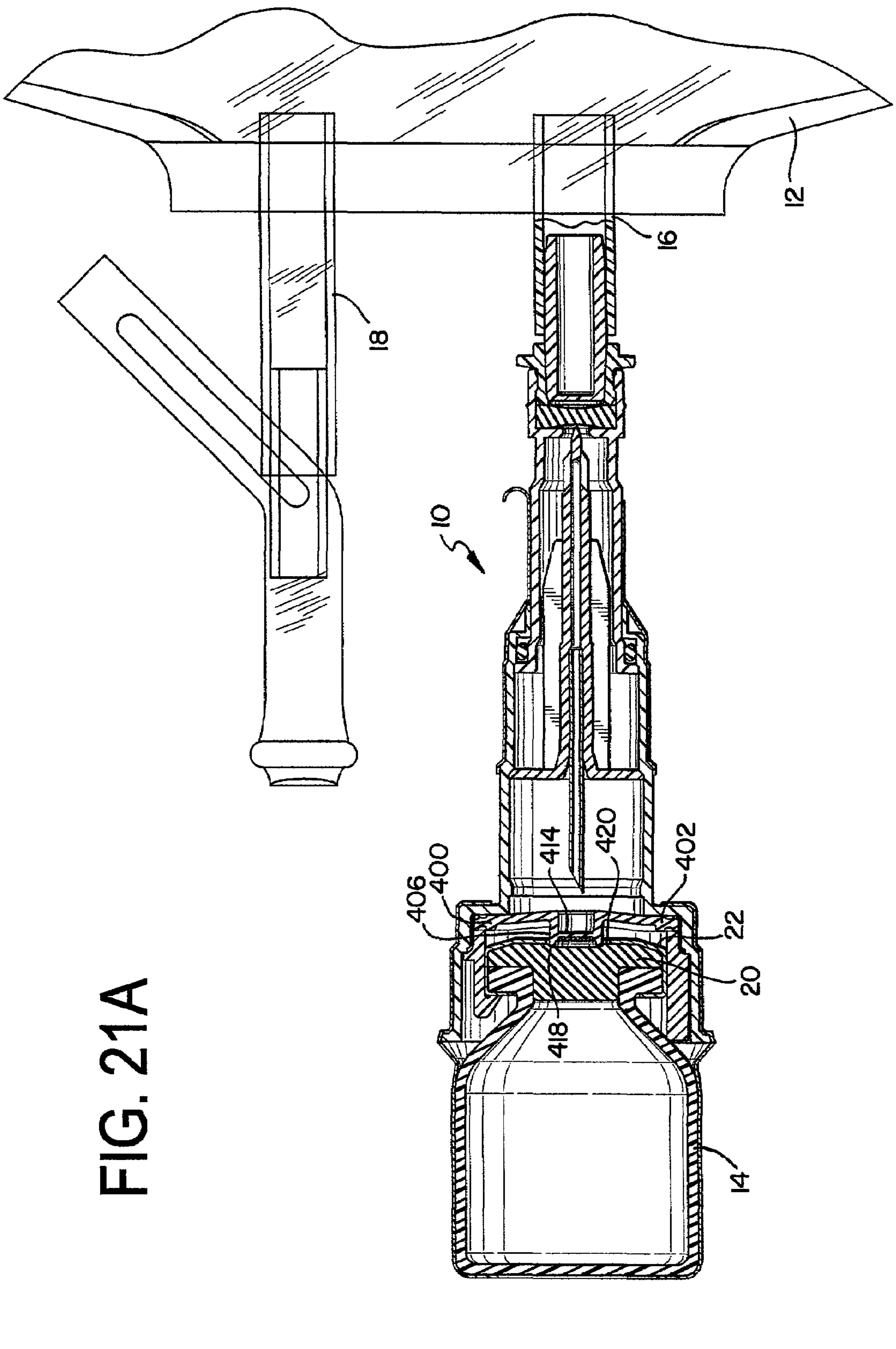
FIG. 21A is a cross-sectional view of the connector device of the present invention utilizing the sealing member of FIG. 19, and having a drug vial fixedly secured to the connector device, the connector device being in an inactivated position.
Figure 21B:
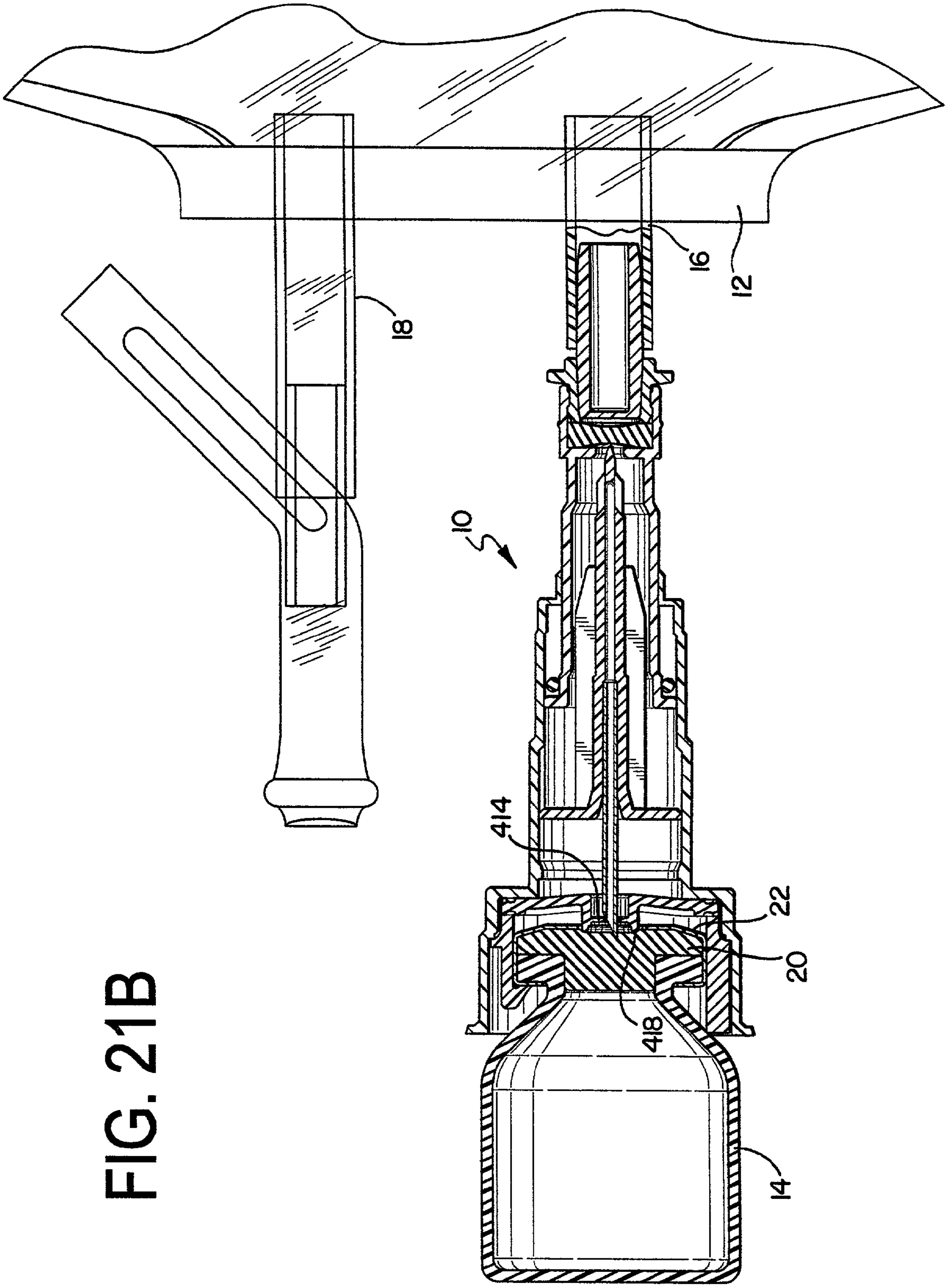
FIG. 21B is a cross-sectional view of the connector device shown in FIG. 21A wherein the connector device is in the initial stages of an activation process.
Figure 21C:
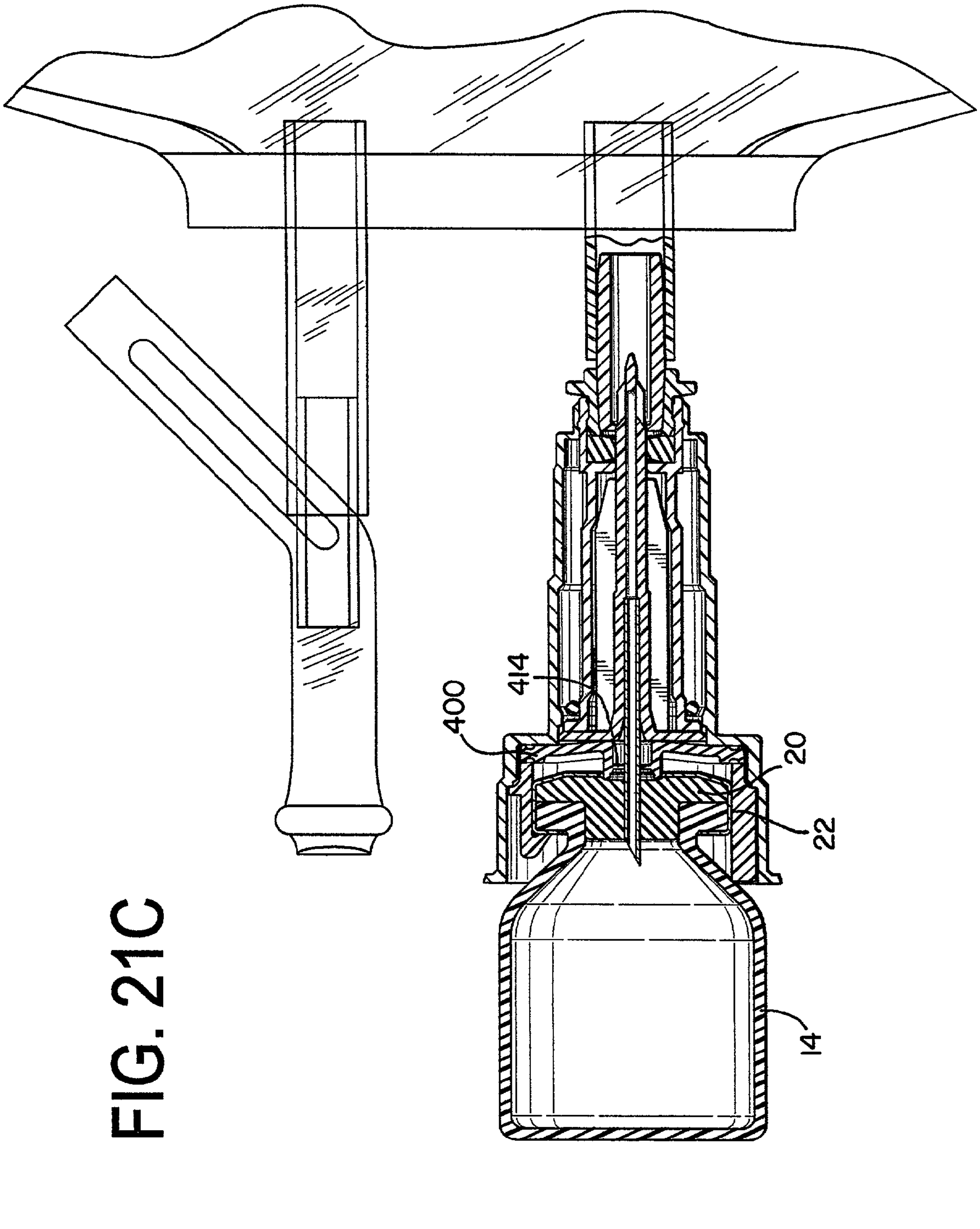
FIG. 21C is a cross-sectional view of the connector device of FIG. 21A in an activated position.
Figure 21D:
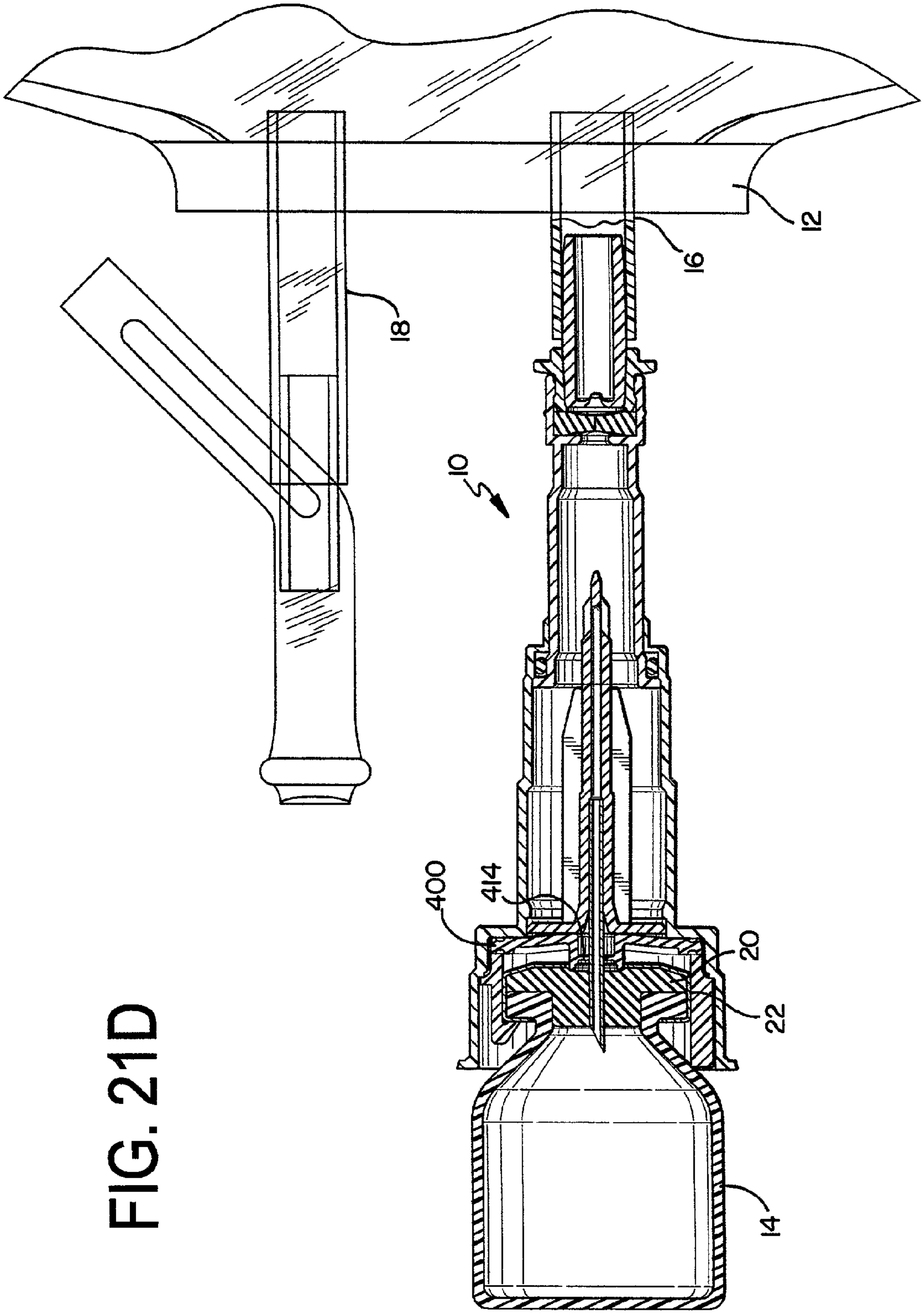
FIG. 21D is a cross-sectional view of the connector device of FIG. 21A in a deactivated position.

FIG. 21A shows the septum 400 connected to the connector 10. The septum 400 is cooperates similarly with the gripper assembly 28 to be mounted in the connector 10 as described above. FIG. 21 also shows the vial 14 connected to the connector 10. The vial 14 has the rubber stopper 20 positioned in the opening of the vial 14 and the crimp ring 22 positioned over the stopper 20. The crimp ring has an aperture that defines the target site 23 on the rubber stopper 20. When the vial 14 is connected to the connector 10, the septum 400 provides a fluid tight seal on the vial 14. In particular, the annular ring 406 abuts the rubber stopper 20 to provide the seal. In particular, the rounded protrusion 418 indents the rubber stopper 20 sufficiently to provide the fluid tight seal. The height of the annular ring 406 is set such that a sufficient interference fit is achieved between the annular ring 406 and the rubber stopper 20. The rounded end of the annular ring 406 assures that the rubber stopper 20 is indented but not cut by the ring 406. As further shown in FIG. 21, the annular ring 406 indents the rubber stopper 20 at the target site 23. The annular ring 406 is spaced inwardly from the crimp ring 22 wherein a space 420 is maintained between the annular ring 406 and the crimp ring 22. As discussed, the membrane 414 is spaced from the rubber stopper 20. After the vial 14 is connected, the connector 10 can be activated as shown in FIGS. 21B and 21C wherein the piercing member 76 pierces through the membrane 414 and rubber stopper 20 and into the vial 14. The connector 10 can also be positioned in the deactivated position shown in FIG. 21D.

With some vials 14, the rubber stoppers 20 used may have imperfections across a top surface of the stoppers 20 The stoppers 20 may have bumps at locations that would correspond to the target site on the stopper. The stoppers 20 may also have identification markings. These imperfections or markings can vary the height of the stopper 20. The rigidity of the septum 400 sufficiently deforms the stopper 20 without piercing the stopper 20 and helps provide a sufficient fluid tight seal regardless of such imperfections or markings across the rubber stopper 20.

Figure 23:
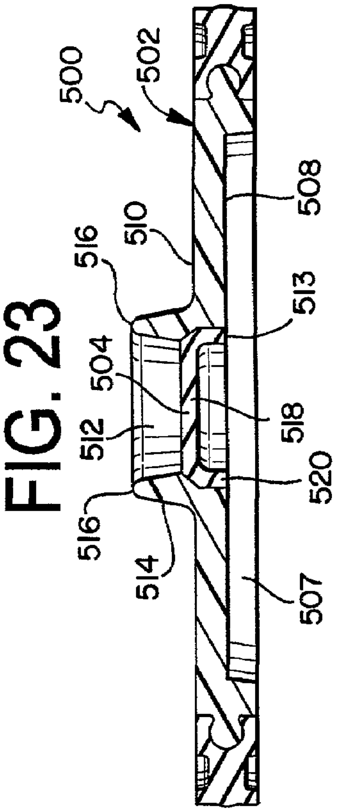
FIG. 23 is a cross-sectional view of the sealing member taken along lines 23—23 in FIG. 22.
Figure 22:
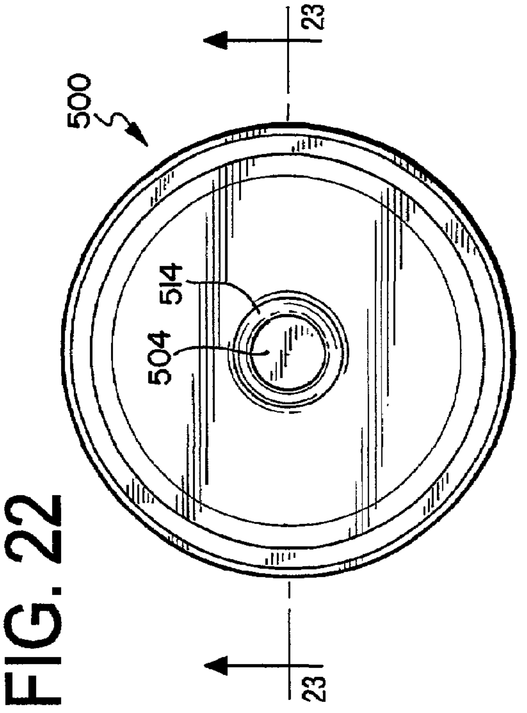
FIG. 22 is a plan view of another embodiment of the sealing member used in the connector device of the present invention.
Figure 24:
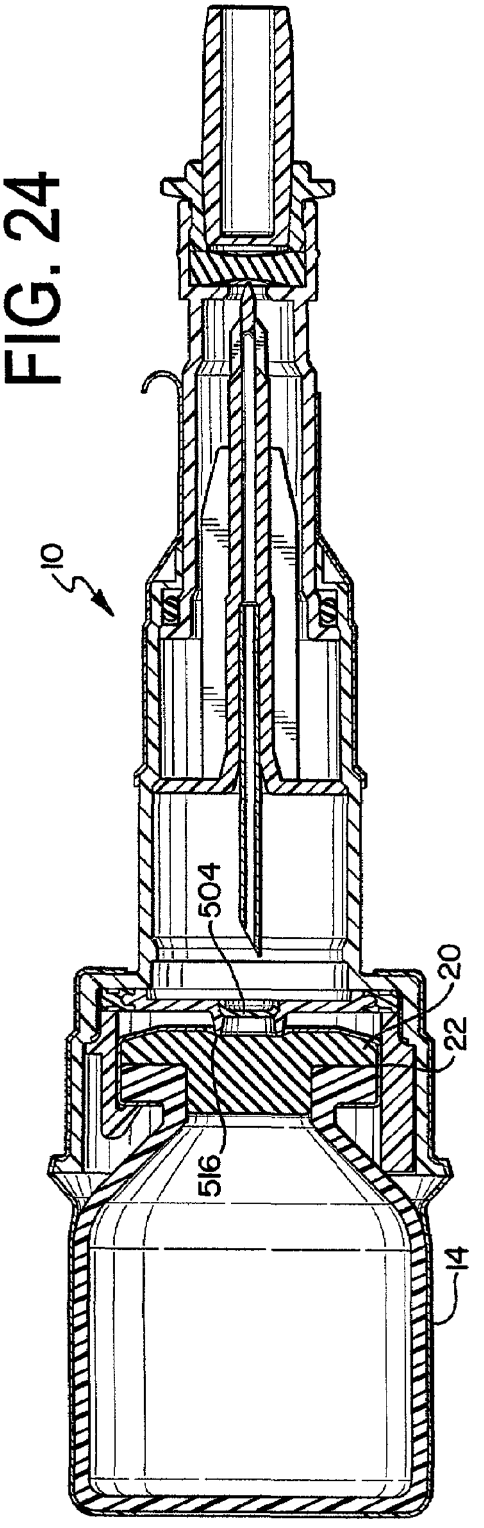
FIG. 24 is cross-sectional view of the connector device of the present invention utilizing the sealing member of FIG. 20.

FIGS. 22–24 disclose yet another embodiment of the sealing member 84, used with the connector device 10, generally designated by the reference numeral 500. Generally, the sealing member 500, or septum 500, has one portion made of rigid material and a pierceable portion made of a rubber material. In one preferred embodiment, the portions of the septum 500 are formed simultaneously together in a two-shot injection molded process. It is understood, however, that other processes can be used to connect the separate portions including an insert molding process. Adhesives or an interference fit could also be used.

As shown in FIGS. 22 and 23, the septum 500 generally has a base 502 and a membrane 504.

As generally shown in FIGS. 22 and 23, the base 502 is generally disk-shaped. The disk or base 502 has a first surface 508 and a second surface 510. The first surface 508 faces into the connector 10 and the second surface 510 faces the container to be attached to the connector 10. The base 502 has an opening 512 therethrough, preferably in a center of the base 502. The opening 512 defines an inner surface 513 on the base 502. The base further has an annular ring 514 extending from the second surface of the base 502 and around the center opening 512. The annular ring 514 is tapered wherein a distal end has rounded protrusion 516. The annular ring 512 is capable of forming a fluid tight seal with the closure 20 of the vial 14 as described below. The first side 508 has a recessed portion 507.

The membrane 504 is positioned in the center opening 512 and closes the opening 512. The membrane has a generally planar section 518 with a depending leg 520. The leg 520 is connected to the inner surface 513 of the base 502.

As further shown in FIGS. 22 and 23, the base 502 has the similar grooved structure as described above for connecting the septum 500 to the gripper assembly 28. In a preferred embodiment, the base 502 may have a collar 522. To that end, the base 502 has an outer peripheral edge 524. The collar 522 is connected to the outer peripheral edge. Specifically, the base 502 has a tongue 526 and the collar has an inner peripheral groove 528. The tongue 526 is received by the groove 528. The collar 522 has the grooved structure as described above. In addition, the collar 522 is formed of the rubber material like the membrane 504.

As discussed, the septum 500 is formed sin one preferred embodiment by a two-shot injection molded process. The base 502 of the septum 500 is a rigid plastic material. The membrane 504 and collar 522 of the septum 500 are a softer rubber material. The components are molded together simultaneously in a two-shot injection molded process as is known in the art. The septum 500 possesses the rigidity from the plastic material that provides a fluid tight seal with the closure while also possessing a soft material in the membrane for the piercing member to easily pierce through.

FIG. 24 shows the septum 500 connected to the connector 10. The septum 500 is cooperates similarly with the gripper assembly 28 to be mounted in the connector 10 as described above. FIG. 24 also shows the vial 14 connected to the connector 10. The vial 14 has the rubber stopper 20 positioned in the opening of the vial 14 and the crimp ring 22 positioned over the stopper 20. The crimp ring has an aperture that defines the target site 23 on the rubber stopper 20. When the vial 14 is connected to the connector 10, the septum 500 provides a fluid tight seal on the vial 14. In particular, the annular ring 514 abuts the rubber stopper 20 to provide the seal. In particular, the rounded protrusion 516 indents the rubber stopper 20 sufficiently to provide the fluid tight seal. The height of the annular ring 514 is set such that a sufficient interference fit is achieved between the annular ring 514 and the rubber stopper 20. The rounded end of the annular ring 516 assures that the rubber stopper 20 is indented but not cut by the ring 406. As further shown in FIG. 24, the annular ring 514 indents the rubber stopper 20 at the target site 23. The annular ring 514 is spaced inwardly from the crimp ring 22 wherein a space 530 is maintained between the annular ring 514 and the crimp ring 22. After the vial 14 is connected, the connector 10 can be activated wherein the piercing member pierces through the membrane 414 and rubber stopper 20 and into the vial 14.

While the specific embodiments have been illustrated and described, numerous modifications come to mind without significantly departing from the spirit of the invention, and the scope of protection is only limited by the scope of the accompanying claim.

We claim:

1. A connector device for establishing fluid communication between a first container and a second container comprising:

a sleeve assembly having a first end and a second end and a cylindrical sidewall, the sidewall having an inner surface and a protuberance integrally formed on the inner surface;

a first attaching member connected to the first end of the sleeve assembly and adapted to attach to the first container;

a second attaching member connected to the second end of the sleeve assembly and adapted to attach to the second container;

a piercing member positioned within the sleeve assembly for providing a fluid flow path from the first container to the second container, the piercing member moveable from a first position in the inactivated position to a second position in the activated position wherein the piercing member moves past the protuberance, the protuberance configured to contact the piercing member to prevent movement of the piercing member back to the first position.

2. The device of claim 1 wherein the sleeve assembly comprises a first sleeve and a second sleeve mounted for translational motion with respect to one another, the first sleeve being connected to the first attaching member and the second sleeve being connected to the second attaching member, the protuberance positioned on the inner surface of the sidewall of the second sleeve.

3. The device of claim 1 wherein the sleeve assembly has a protrusion on the inner surface at the first end, the first attaching member comprises a port connector having a port snap connected to a port sleeve, the port snap having a flange extending from an outer surface, the port connector being connected to the first end of the sleeve assembly wherein the flange engages the protrusion, the port sleeve adapted to attach to the first container.

4. The device of claim 3 wherein the port sleeve has a membrane at one end.

5. The device of claim 3 further comprising a sealing member positioned at the first end of the sleeve assembly adjacent the port snap.

6. The device of claim 1 wherein the second attaching member comprises a gripper assembly attached to the second end of the sleeve assembly, the gripper assembly having a base and an annular wall portion extending from the base and a plurality of fingers circumjacent the wall portion, the fingers being circumferentially spaced defining a vial receiving chamber adapted to receive the vial, wherein one finger has a tab adapted to engage an underside of the neck and one finger has a standing rib adapted to engage a side portion of the vial closure.

7. The device of claim 6 wherein the gripper assembly further has a first annular rim extending from the base and a second annular rim extending collectively from the fingers and in spaced relation to the first annular rim.

8. The device of claim 7 further comprising a septum having a disk having opposing first and second surfaces, the first surface having a first annular groove receiving the first annular rim, the second surface having a second annular groove receiving the second annular rim.

9. The device of claim 8 wherein the second surface of the septum further has an annular ridge having a sidewall tapering axially-outwardly, so that the annular ridge is capable of forming a fluid tight seal with the vial when the vial is received by the fingers of the gripper assembly.

10. The device of claim 8 wherein the disk has a center hub having a generally thickened cross-section.

11. The device of claim 6 wherein the wall portion has a lip at a peripheral end, the device further comprising an end cap releasably secured to the gripper assembly and cooperating with the lip.

12. The connector device of claim 1 wherein the piercing member has a first end and a second end and further comprising means for independently hermetically sealing the first and second ends of the piercing member.

13. The device of claim 1 further comprising a septum positioned over the second end of the sleeve assembly, the septum having a center hub having a generally thickened cross-section.

14. The device of claim 1 further comprising a tamper evident strip positioned around the sleeve assembly.

15. The device of claim 1 wherein the sleeve assembly is movable from the inactivated position to the activated position by a force generally applied to the device outside the first container.

16. The device of claim 1 wherein the sleeve assembly has a projection that maintains the piercing member in the first position when the device is in the inactivated position.

17. The device of claim 1, wherein the piercing member includes an extended diameter portion, the protuberance preventing, via contact with the extended diameter portion, movement of the piercing member back to the first position.

18. A connector device for establishing fluid communication between a first container and a second container comprising:

a first cylindrical sleeve member having a first end and a second end;

a first attaching member on the first end of the first sleeve cylindrical member and adapted to attach to the first container;

a second cylindrical sleeve member having a first end and a second end, the second sleeve member being associated with the first cylindrical sleeve member and is movable axially with respect thereto from an inactivated position to an activated position, the second cylindrical sleeve member having a protuberance integrally formed on an inner surface of the second cylindrical sleeve member;

a second attaching member on the second end of the second cylindrical sleeve member and adapted to attach the second cylindrical sleeve member to the second container;

a piercing member positioned within the second cylindrical sleeve member for providing a fluid flow path between the first container and the second container, the piercing member moveable from a first position in the inactivated position to a second position in the activated position wherein the piercing member contacts and moves past the protuberance, the protuberance configured to contact the piercing member to prevent movement of the piercing member back to the first position.

19. The device of claim 18, wherein the piercing member includes a hub, wherein the hub of the piercing member contacts and moves past the protuberance.

* * * * *